(12) United States Patent
Bhatia et al.

(10) Patent No.: US 7,332,153 B2
(45) Date of Patent: *Feb. 19, 2008

(54) COSMETIC COMPOSITIONS

(75) Inventors: Shameem Bhatia, Wirral (GB); Jan van Esch, Groningen (NL); Colette Marie Fairclough, Wirral (GB); Kevin Ronald Franklin, Wirral (GB); Paul Hugh Findlay, Wirral (GB); Nicholas Webb, Wirral (GB); Michael Stephen White, Wirral (GB)

(73) Assignee: Unilever Home & Personal Care USA Division of Conopco, Inc., Chicago, IL (US)

( * ) Notice: Subject to any disclaimer, the term of this patent is extended or adjusted under 35 U.S.C. 154(b) by 283 days.

This patent is subject to a terminal disclaimer.

(21) Appl. No.: 10/346,646

(22) Filed: Jan. 17, 2003

(65) Prior Publication Data
US 2003/0180239 A1 Sep. 25, 2003

(30) Foreign Application Priority Data

Jan. 18, 2002 (GB) .................................. 0201164.1
Aug. 1, 2002 (GB) .................................. 0217840.8

(51) Int. Cl.
*A61K 8/18* (2006.01)
*A61K 8/00* (2006.01)
*A61Q 15/00* (2006.01)

(52) U.S. Cl. .......................... 424/65; 424/66; 424/67; 424/68; 424/401; 514/11; 514/255.02

(58) Field of Classification Search .................. 514/9, 514/11, 255.02, 944; 424/65–68, 400, 401; 516/915

See application file for complete search history.

(56) References Cited

U.S. PATENT DOCUMENTS

| | | | |
|---|---|---|---|
| 3,969,087 A | 7/1976 | Saito et al. ........................ 44/7 |
| 4,725,430 A | 2/1988 | Schamper et al. ............. 424/66 |
| 4,725,432 A | 2/1988 | May .............................. 424/66 |
| 4,822,602 A | 4/1989 | Sabatelli ....................... 424/65 |
| 4,954,333 A | 9/1990 | Ward ............................ 424/66 |
| 5,169,626 A | 12/1992 | Tanner et al. ................. 424/66 |
| 5,232,689 A | 8/1993 | Katsoulis et al. ............. 424/66 |
| 5,348,117 A | 9/1994 | Pickering ........................ 182/5 |
| 5,455,026 A | 10/1995 | Bahr et al. .................... 424/65 |
| 5,492,691 A | 2/1996 | Bahr et al. .................... 404/65 |
| 5,750,096 A | 5/1998 | Guskey ......................... 424/65 |
| 5,863,525 A * | 1/1999 | Angelone et al. ............. 424/66 |
| 6,231,841 B1 | 5/2001 | Franklin et al. .............. 424/65 |
| 6,248,312 B1 | 6/2001 | Franklin et al. .............. 424/65 |
| 6,251,377 B1 | 6/2001 | Franklin ....................... 424/65 |
| 6,372,235 B1 | 4/2002 | Livoreil et al. .............. 424/401 |
| 6,410,001 B1 | 6/2002 | Franklin et al. .............. 424/65 |
| 6,410,003 B1 | 6/2002 | Bhatia et al. ................. 424/65 |
| 6,458,344 B2 | 10/2002 | Franklin et al. .............. 424/65 |
| 2004/0223994 A1* | 11/2004 | Emslie et al. ................. 424/401 |
| 2004/0223995 A1* | 11/2004 | Emslie et al. ................. 424/401 |

FOREIGN PATENT DOCUMENTS

| | | |
|---|---|---|
| EP | 665 007 | 8/1995 |
| EP | 512 770 | 10/1996 |
| EP | 1 068 854 | 1/2001 |
| EP | 1 177 784 | 2/2002 |
| JP | 10226615 A * | 8/1998 |
| WO | 92/19222 | 11/1992 |
| WO | 93/23008 | 11/1993 |
| WO | 98/27954 | 7/1998 |
| WO | 00/61079 | 10/2000 |
| WO | 01/58411 | 8/2001 |
| WO | 02/11692 | 2/2002 |

OTHER PUBLICATIONS

Abrutyn, E.S., "Formulating Enhancements for Underarm Applications," 1993, Cosmetic Toiletries, 108 (7) (abstract).*
English language translation of JP 10-226615, published Aug. 25, 1998.*
Mohamed Mostafa Badawi, Synthesis of Peptide Amides by Ammonolysis of Peptide Resins, 1971, Journal of Drug Research, vol. 3, No. 1-2, pp. 223-230.*
Smith et al, Solid-Phase Synthesis of a Library of Piperazinediones and Diazepinediones via Kaiser Oxime Resin, 1998, Bioorganic and Medicinal Chemistry Letters, vol. 8, pp. 2369-2374.*
Suzuki et al, Acetic Acid-Catalyzed Diketopiperazine Synthesis, 1981, Chem. Pharm. Bull., vol. 29, No. 1, pp. 233-237.*

(Continued)

*Primary Examiner*—Sreeni Padmanabhan
*Assistant Examiner*—Kendra D. Carter
(74) *Attorney, Agent, or Firm*—Karen E. Klumas

(57) ABSTRACT

Cosmetic formulations containing a cosmetic active and a continuous phase comprising a water-immiscible liquid carrier, such as, amongst other materials, silicone oils, branched aliphatic alcohols or liquid aromatic/aliphatic esters that is structured by a cyclodipeptide derivative having the general formula

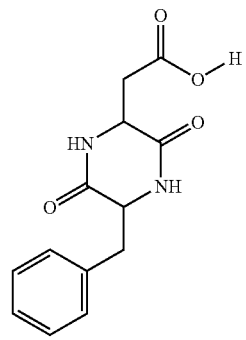

in which $R_A$ represents a carbocyclic or heterocyclic group containing not more than 2 rings, other than unsubstituted cyclohexyl.

58 Claims, No Drawings

OTHER PUBLICATIONS

Cosmetics & Toiletries, *"Deodorant/Antiperspirant—Sticks"*, vol. 105, Apr. 1990 (pp. 75-78).

J. Chem. Society Chemical Commun., 1994 *"Cyclo(dipeptide)s as Low-molecular-mass Gelling Agents to harden Organic Fluids"*, Hanabusa et al., (pp. 1401-1402).

Journal of Colloid and Interface Science 224, *"Low Molecular Weight Gelators for Organic Fluids: Gelation Using A Family of Cyclo(dipeptide)s"*, Hanabusa et al., (pp. 231-244), 2000.

Co-pending Application: Fairlough et al., U.S. Appl. No. 10/346,676, filed: Jan. 17, 2003.

Co-pending Application: Franklin; U.S. Appl. No. 10/346,677, filed: Jan. 17, 2003.

Great Britain Search Report in a GB application GB 0201163.3.

Great Britain Search Report in a GB application GB 0217840.8.

Great Britain Search Report in a GB application GB 0201164.1.

Caplus Abstract Accession No. 1998: 599614 & JP 100245315 A2 (Pola Chemical Industries) Sep. 14, 1998.

Caplus Abstract Accession No. 2001:668189 & JP 2001247451 A2 (Pola Chemical Industries Inc. & Nisshin Oils Mills Ltd.) Sep. 11, 2001.

Caplus Abstract Accession No. 1998:555702 & JP 10226615 A2 (Pola Chemical Industries Inc.) Aug. 25, 1998.

* cited by examiner

COSMETIC COMPOSITIONS

FIELD OF THE INVENTION

The present invention relates to cosmetic compositions for application to human skin, to the preparation and use of such compositions and to structurants for incorporation in such compositions and their preparation.

BACKGROUND OF THE INVENTION AND SUMMARY OF PRIOR ART

A wide variety of cosmetic compositions for application to human skin make use of a structured liquid carrier to deliver colour or some other active material to the surface of the skin. Significant examples of such cosmetic compositions include antiperspirant or deodorant compositions which are widely used in order to enable their users to avoid or minimise wet patches on their skin, especially in axillary regions or to control or prevent the emission of malodours, which could otherwise arise when the user perspires. Other examples of cosmetic compositions include lip sticks.

Although structuring is a term that has often been employed in respect of materials which structure a carrier liquid, various other terms have been employed alternatively, including solidifying and gelling.

Antiperspirant or deodorant formulations have been provided with a range of different product forms. One of these is a so-called "stick" which is usually a bar of an apparently firm solid material held within a dispensing container and which retains its structural integrity and shape whilst being applied. In that respect they are representative of cosmetic compositions in stick form containing other active constituents. When a portion of the stick is drawn across the skin surface, a film of the stick composition is transferred to the skin surface. Although the stick has the appearance of a solid article capable of retaining its own shape for a period of time, the material often has a structured liquid phase so that a film of the composition is readily transferred from the stick to another surface upon contact.

Antiperspirant sticks can be divided into three categories. Suspension sticks contain a particulate antiperspirant active material suspended in a structured carrier liquid phase which often is anhydrous and/or in many instances may be water-immiscible. Emulsion sticks normally have a hydrophilic phase, commonly containing the antiperspirant active in solution, this phase forming an emulsion with a second, more hydrophobic, liquid phase. The continuous phase of the emulsion is structured. Solution sticks typically have the antiperspirant active dissolved in a structured liquid phase which is polar and may comprise a polar organic solvent, which is often water-miscible, and the polar phase can contain water.

There is substantial literature on structuring of cosmetic compositions, for example as represented by antiperspirant or deodorant compositions.

Conventionally, many sticks have been structured using naturally-occurring or synthetic waxy materials, in which term we include materials which resemble beeswax, in that they soften progressively with increase in temperature until they are fluid, generally by about 95° C. Examples of wax-structured sticks are described in an article in Cosmetics and Toiletries, 1990, Vol 105, P75-78, in U.S. Pat. Nos. 5,169,626 and 4,725,432 and in many other publications, in some of which such materials are called solidifying agents.

More specifically, it has been common practice for sticks to be structured or solidified by incorporating fatty alcohol into the composition, often accompanied by a smaller amount of castor wax. Sticks which are structured with fatty alcohol tend to leave visible white deposits on application to human skin; moreover the deposits can also transfer onto clothing when it comes into contact with the skin and the wearer can, for example, find white marks at the armhole of the sleeveless garment. Fatty alcohols are often regarded as coming within the general category of waxy materials, but we have observed that they are a more significant source of white deposits than various other waxy materials.

Some alternative structurants or solidifying agents to waxy materials have been proposed. For example, the use of dibenzylidene sorbitol (DBS) or derivatives thereof as gellant for a polar or hydrophylic carrier liquid has been proposed in a number of publications such as EP-A-512770, WO-92/19222, U.S. Pat. Nos. 4,954,333, 4,822,602 and 4,725,430. Formulations containing such gellants can suffer from a number of disadvantages, including instability in the presence of acidic antiperspirants, and comparatively high processing temperatures needed in the production of sticks.

Other alternative proposed structurants include various classes of esters or amides that are solid at ambient temperature and are capable of solidifying a hydrophobic or water-immiscible liquid carrier. One such class comprises ester or amide derivatives of 12-hydroxystearic acid, as described in inter alia U.S. Pat. No. 5,750,096. Another class of such esters or amides comprises N-acyl amino acid amides and esters, of which N-Lauroyl-L-glutamic acid di-n-butylamide is commercially available from Ajinomoto under their designation GP-1. They are described in U.S. Pat. No. 3,969,087. A further class which has been disclosed as gelling agents comprises the amide derivatives of di and tribasic carboxylic acids set forth in WO 98/27954 notably alkyl N,N'-dialkyl succinamides. Yet other amide structurants for water-immiscible liquid carriers are described in EP-A-1305604.

Although many amido-structurants have been identified already, it remains an objective to locate others which may meet the exacting standards of the cosmetic industry and ameliorate or eliminate one or more of the difficulties or disadvantages associated with the various amido structurants that have already been proposed or used.

One further class of compounds which contain a —CO—NH— group comprises cyclodipeptides, which are cyclic derivatives of aminoacids. Various cyclodipeptides has been described in an article by K Hanabusa et al entitled Cyclo (dipeptide)s as low molecular-mass Gelling Agents to harden Organic Fluids, J. Chem Soc. Commun., 1994 pp1401/2. The cyclodipeptides satisfied the general formula

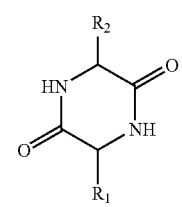

in which $R_1$ and $R_2$ are designated organic residues. The selection exemplified included two materials (8 and 9) in which $R_1$ represented alkyl esters, being either —$CH_2CO_2CH_2CH_2CH_2Me$ or —CH$_2$CO$_2$CH$_2$CH$_2$CHMeCH$_2$CH$_2$CH$_2$CHMe$_2$ and R$_2$ represented —CH$_2$Ph. This paper is herein referred to as Hanabusa I.

In an introductory section, Hanabusa states that the most difficult problem for the development of low molecular mass gelling agents is how to stabilise the formed gel, in other words how to prevent the transformation from the metastable gel to a crystalline state. Having conducted an extensive research programme into gels formed using low molecular mass gellants, the Applicants are able to confirm that the stabilisation of such gels often does indeed represent a serious and difficult problem, and indeed a problem that can be exacerbated in cosmetic compositions by the presence of other cosmetic ingredients. Hanabusa I subsequently makes a general assertion that the formed gels (sic. employing the exemplified cyclodipeptides in the list of organic fluids given in Table 1) were stable even after several months.

Various other cyclo(dipeptides) satisfying formula 1 above were described in a second article by Hanabusa et al entitled Low Molecular Weight Gelators for Organic Fluids: Gelation using a Family of Cyclo(dipeptide)s, in the Journal of Colloid and Interface Science 224, 231-244 (2000), herein called Hanabusa II. The text disclosed materials no 22 to 28, which were further esters like those of materials 8 and 9 in Hanabusa I, except that they were derived from different alkanols. Applicants have found that such esters, and in particular 27 and 28 in Hanabusa II, produced gels that were only poorly stable.

Applicants tested a number of materials as gellants in oils that are common in cosmetic formulations in accordance with Formula 1 in Hanabusa I, II-27 and II-28, which seemed to be Hanabusa's best gellants. Unfortunately, the resultant products demonstrated inferior storage characteristics, at laboratory ambient temperatures. Applicants deduced that at best, the capability of cyclodipeptides to gel organic fluid stably could vary significantly, depending on the chemical nature of the substituent residues R$_1$ and R$_2$.

A number of cyclic dipeptide derivatives have been described as gellants in Japanese Kokai No 2001-247451, in the name of Pola Chemical Industries Inc and Nisshin Oil Mills Ltd. These were either alkyl derivatives, which had already been described by Hanabusa or the unsubstituted cyclohexyl derivative which likewise showed inferior stability when tested in the same manner as those proposed by Hanabusa.

SUMMARY OF THE INVENTION

Applicants have now found that selected cyclodipeptide derivatives can be used as structurants for cosmetic compositions. When used as a modest percentage of the composition, typically not more than 15% by weight and often less than 10% by weight, they are able to structure the composition in a manner that is superior to that achieved by material II-27 and II-28 of Hanabusa. Indeed, at the same time, and where appropriate, the composition can yield a deposit with no worse than a low visible residue. It will be recognised that cyclodipeptide derivatives herein may alternatively be called diketopiperazine derivatives.

It is an object of the present invention to provide structured cosmetic compositions, in which a liquid carrier material is structured using a structuring agent which is different from those mentioned above. A further object of the invention is to provide a structurant which can exhibit a superior property to at least structurants II-27 and II-28 of Hanabusa identified above.

A yet further object of some embodiments of the invention is to provide compositions which exhibit low visible deposits.

It has been found that the properties of gels in hydrophobic carrier liquids can be improved by esterifying a cyclo (dipeptide) acid with an alcohol producing a cyclic residue.

Broadly, in a first aspect of the present invention, there is provided a cosmetic composition comprising:
(i) an antiperspirant active material
(ii) a continuous phase which comprises water-immiscible liquid carrier, and
(ii) a structurant therein which comprises a cyclodipeptide derivative having the general formula

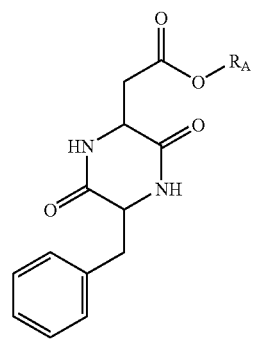

in which R$_A$ represents a carbocyclic or heterocyclic group containing not more than 2 rings, other than unsubstituted cyclohexyl.

Such cyclodipeptide compounds are sometimes referred to herein as DOPA derivatives or DOPAD and the residue containing the cyclodipeptide and the carboxyl group is sometimes called herein a DOPA residue.

For the avoidance of doubt, in the DOPA derivatives employed herein, the cyclic group within R$_A$ is directly bonded to the DOPA residue.

A DOPA derivative as above serves as a structuring agent for the water-immiscible liquid carrier and when used in a sufficient amount, which is likely to be less than 15% of the total composition, is able to structure this liquid into a gel with sufficient rigidity to sustain its own shape.

We have observed that the structuring compounds used in this invention form fibres or strands within the liquid phase. Without being bound to any specific theory or explanation, we believe that upon gel formation a network of such fibres is formed which extends throughout the liquid phase. Upon heating the gel to the gel melting temperature, the strands of structurant dissolve and the liquid phase becomes more mobile.

In order to promote good sensory properties at the time of use it is preferred to include a silicone oil as at least a fraction of the water-immiscible carrier liquid. The amount of silicone oil may be at least 10% by weight of the composition and/or at least 25% by weight of the water-immiscible carrier liquid.

Fatty alcohols which are solid at room temperature of 20° C., such as stearyl alcohol, lead to deposits with an opaque white appearance and are preferably substantially absent, by which we mean present in an amount of no more than 3% by weight of the composition, more preferably less than 1% and most preferably 0%. As already mentioned, fatty alcohols are often regarded as coming within the general category of waxy materials. More generally the term "wax" is conventionally applied to a variety of materials and mixtures (including some fatty alcohols) which have some diversity in chemical structure but similarity in physical properties. The term generally denotes materials which are solid at 30° C., often also solid up to 40° C., having a waxy appearance or feel, but which gradually soften and eventually melt to a mobile liquid at a temperature below 95° C. usually below 90° C.

Possibly the composition does not include more than 3% of any material which is a wax, ie a solid at 30° C. but softens at an elevated temperature and at 95° C. is molten and soluble in the water-immiscible liquid, yet which is unable to form a network of fibres therein on cooling to 20° C.

As will be explained in more detail below, in cosmetic compositions herein, the structured water-immiscible carrier liquid may be the continuous phase in the presence of a dispersed second phase, which may comprise a suspension of particulate solid forming a suspension stick or a dispersion of droplets of a lypohobic liquid. Such a solid may be a particulate antiperspirant or deodorant active or pigment. Such a disperse liquid phase may comprise a solution of the aforementioned active or actives in water or other hydrophilic ie lypohobic solvent.

Further advantages of preferred structurant materials of this invention are that the gels they produce are physically more stable, both during processing and in the resultant compositions, by comparison with gellants II-27 and II-28 of Hanabusa.

A composition of this invention will generally be marketed in a container by means of which it can be applied at time of use. This container may be of conventional type.

A second aspect of the invention therefore provides a cosmetic product comprising a dispensing container having an aperture for delivery of the contents of the container, means for urging the contents of the container through the said aperture, and a composition of the first aspect of the invention in the container.

Means for urging the contents of the container to the said aperture or apertures, for flow through them, may be moving parts operable by the user or an orifice in the container opposite the aperture providing digital access.

The compositions of this invention can be produced by conventional processes for making cosmetic solids.

Thus, according to a third aspect of the present invention there is provided a process for the production of a cosmetic composition comprising the steps of:
   a1) incorporating into a water-immiscible liquid carrier a structurant which is one or more structurant compounds as defined in the first aspect,
   a2) mixing the liquid carrier with a solid or a disperse liquid phase comprising cosmetic active in particulate or dissolved form to be suspended in the water-immiscible liquid,
   a3) heating the liquid carrier or a mixture containing it to an elevated temperature at which the structurant is dissolved or dispersed in the water-immiscible liquid carrier,
   steps a1) a2) and a3) being conducted in any order followed by:
   b1) introducing the mixture into a mould which preferably is a dispensing container, and then
   c1) cooling or permitting the mixture to cool to a temperature at which the liquid carrier is solidified.

A suspended solid may be any cosmetic active that is at least partly insoluble in the lypohilic water-immiscible liquid carrier in the amount incorporated therein and a disperse liquid phase may be a solution of such an active in a hydrophilic or polar solvent.

In a fourth aspect of the present invention, the cosmetic active comprises an antiperspirant or deodorant active. According to the fourth aspect, there is provided a cosmetic method for preventing or reducing perspiration or odour formation on human skin comprising topically applying to the skin a composition comprising an antiperspirant or deodorant active, a water-immiscible liquid carrier and a structurant compound as defined above in the first aspect.

In a fifth aspect of the present invention there are provided novel ester derivatives of DOPA according to the general formula given in the first aspect.

In a sixth aspect of the present invention there is provided a process for making the novel esters of the fifth aspect in which DOPA acid is reacted with at least an equimolar amount of an alcohol of formula $R_AOH$ in the presence of at least 0.5 moles of promoter per mole of DOPA acid in a reaction medium comprising dimethyl sulphoxide.

DETAILED DESCRIPTION AND EMBODIMENTS

As mentioned hereinabove, in accordance with the first aspect, the invention requires a structurant compound within a water-immiscible liquid phase. Other materials may also be present depending on the nature of the composition. The various materials will now be discussed by turn and preferred features and possibilities will be indicated.

The structurant compounds of the present invention satisfy the general formula:

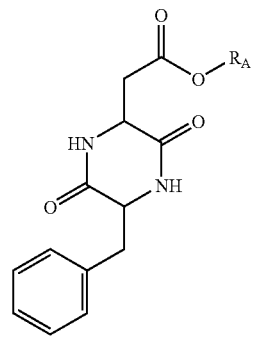

in which $R_A$ represents a carbocyclic or heterocyclic group containing not more than 2 rings, other than unsubstituted cyclohexyl.

Desirably, the carbocyclic or heterocyclic group in $R_A$ is substituted by at least one alkyl, ether or ester substituent and/or contains at least one degree of ring unsaturation. The ring unsaturation may result in a non-aromatic group, for example comprising 1 or 2 degrees of unsaturation or an aromatic group. Although gels made using the derivative in which $R_A$ represents an unsubstituted cyclohexyl group are relatively unstable during storage under normal storage conditions, stability can be improved by distributing one or more substituents around the cyclohexyl group or by introducing unsaturation or a hetero atom.

Herein, $R_A$ can comprise two fused rings, but preferably comprises a single six membered ring, either carbocyclic or heterocyclic, or a bridged ring. When A is carbocyclic, it can be either saturated or unsaturated, preferably unsaturated or aromatic. When $R_A$ is heterocyclic, it is preferably saturated.

Although the cyclic group within $R_A$ can be unsubstituted, with the exception of cyclohexyl, it is preferably substituted by at least one alkyl substituent, which preferably contains no more that 16 carbon atoms. In some highly desirable embodiments the alkyl substituent has a longest chain length of up to 4 carbon atoms, and in certain or those a total carbon content of up to 5 carbon atoms. The alkyl substituent may be linear or branched. Preferred examples include methyl, ethyl, propyl, isopropyl, butyl isobutyl or t-butyl or isopentyl. In a number of very suitable DOPA derivatives, $R_A$ contains two or more alkyl substituents and especially those selected from the above list of preferred examples. The alkyl substituents may be the same, such as two or more methyl substituents, or may be a combination of different substituents such as a methyl and isopropyl substituents. When $R_A$ is saturated, the substituents may depend from the same carbon atom in the ring, such as two methyl groups, or from different carbon atoms. In several highly desirable derivatives, two alkyl substituents are meta or para to each other, for example meta methyl groups or a para methyl and isopropyl group. In yet other derivatives, the ring may include a methylene bridge, which preferably likewise completes a six membered ring.

In some suitable DOPA derivatives, the or one alkyl substituent may be ortho or para to the bond with the DOPA residue, as in 4-methyl-phenyl-. In some or other DOPA derivatives, the bond with the DOPA residue is meta to one or preferably two methyl substituents.

When $R_A$ is heterocyclic, the heterocyclic atom is suitably nitrogen. Conveniently, the heterocyclic atom can be para to the bond with the DOPA residue. Moreover, in a number of desirable derivatives, the heteroatom is ortho to at least one alkyl group, better in a saturated ring and especially to up to 4 ortho methyl groups.

The group $R_A$ is often most easily referred to as the residue from the corresponding alcohol which may be reacted with DOPA to form the ester linkage. Thus, desirable examples of $R_A$ include the residues from 4-alkyl phenol, such as 4-nonyl-phenol, and 2,6-dialkyl- or 2,2,6,6-tetraalkyl-4-piperidinol, such as 2,2,6,6-tetramethyl-4-piperidinol.

In some especially preferred DOPA derivatives, the ring in $R_A$ is carbocyclic, and is substituted by at least two alkyl groups of which at least one is methyl and the other or one of the others is isopropyl. Examples of such $R_A$ residues include menthol, thymol, isopinocamphenol and 3,5-dialkyl cyclohexanol such as 3,5-dimethyl cyclohexanol. Especially desirably, the methyl group is para to the isopropyl group as in the derivatives from carvacrol. The DOPAD from thymol is particularly suitable, because of its capability to form hard, clear and stable sticks.

Although many suitable DOPAD compounds described herein are substituted by an alkyl substituent or substituents, at least one of the substituents can itself be ethylinically unsaturated ie comprise an alkenyl group which in many instances contains from 2 to 6 carbons. Suitable examples include isopropenyl and isobutenyl. Such an unsaturated group may be employed instead of the corresponding saturated alkyl group containing the same number of carbon atoms as described hereinabove. One suitable DOPAD compound comprises the derivative from carveol.

In further compositions, the DOPAD compound may be substituted by an ether or ester, particular in respect of aromatic derivatives, such as benzoate esters. Such esters typically contain up to 10 carbons in the ester substituent. Suitable DOPAD groups containing an ester substituent include ethyl benzoate, butyl benzoate, and hexyl benzoate.

The DOPA derivatives used in this invention may be a mixture of compounds within the general formulae given, or may be a single compound.

These DOPA derivatives can be prepared by reacting the respective alcohol with DOPA in acid form (DOPAA), or possibly with an acid chloride, or possibly an anhydride or an ester containing a DOPA residue. DOPAA can be obtained by cyclising aspartame.

The amount of the said DOPA derivatives in a composition of this invention is likely to be from 0.1 to 15% by weight of the whole composition and preferably from 0.1 up to 10%, and more commonly at least 0.3% and in many instances not more than 5%. In some especially desirable embodiments, the amount of DOPA structurant is from 0.5% to 3.5%. Herein, unless other wise stated, a % is by weight based on the entire composition. If the composition is an emulsion with a separate disperse phase, the amount of structurant compound(s) is likely to be from 0.15 to 20% by weight of the continuous phase, more likely from 0.4% to 8% of this phase. In some highly desirable embodiments the hydrophobic carrier phase contains from 1.5 to 4.5% by weight based on that phase of the DOPAD. It will be recognised that the invention DOPA structurants are particularly advantageous because they are able to produce hard gels at even low concentrations of structurant. This is beneficial, not only because reduces the cost of the structurant, often a relatively expensive ingredient, but also releases formulation space for incorporating other desirable ingredients in the composition and reduces the amount of ingredient which might contribute to visible deposits. Use of a smaller amount of structurant can also assist during the preparation of gelled compositions, offering more flexibility to the step forming a carrier liquid with well dispersed or dissolved gellant.

Carrier Liquid

The water-immiscible carrier liquid comprises one or a mixture of materials which are relatively hydrophobic so as to be immiscible in water. Some hydrophilic liquid may be included in the carrier, provided the overall carrier liquid mixture is immiscible with water. It will generally be desired that this carrier is liquid (in the absence of structurant) at temperatures of 15° C. and above. It may have some volatility but its vapour pressure will generally be less than 4 kPa (30 mmHg) at 25° C. so that the material can be referred to as an oil or mixture of oils. More specifically, it is desirable that at least 80% by weight of the hydrophobic carrier liquid should consist of materials with a vapour pressure not over this value of 4 kPa at 25° C.

It is preferred that the hydrophobic carrier material includes a volatile liquid silicone, i.e. liquid polyorganosiloxane. To class as "volatile" such material should have a measurable vapour pressure at 20 or 25° C. Typically the vapour pressure of a volatile silicone lies in a range from 1 or 10 Pa to 2 kPa at 25° C.

It is desirable to include volatile silicone because it gives a "drier" feel to the applied film after the composition is applied to skin.

Volatile polyorganosiloxanes can be linear or cyclic or mixtures thereof. Preferred cyclic siloxanes include polydimethylsiloxanes and particularly those containing from 3 to 9 silicon atoms and preferably not more than 7 silicon atoms and most preferably from 4 to 6 silicon atoms, otherwise often referred to as cyclomethicones. Preferred linear siloxanes include polydimethylsiloxanes containing from 3 to 9 silicon atoms. The volatile siloxanes normally by themselves exhibit viscosities of below $10^{-5}$ m$^2$/sec (10 centistokes), and particularly above $10^{-7}$ m$^2$/sec (0.1 centistokes), the linear siloxanes normally exhibiting a viscosity of below $5 \times 10^{-6}$ m$^2$/sec (5 centistokes). The volatile silicones can also comprise branched linear or cyclic siloxanes such as the aforementioned linear or cyclic siloxanes substituted by one or more pendant —O—Si(CH$_3$)$_3$ groups. Examples of commercially available silicone oils include oils having grade designations 344, 345, 244, 245 and 246 from Dow Corning Corporation; Silicone 7207 and Silicone 7158 from Union Carbide Corporation; and SF1202 from General Electric.

The hydrophobic carrier employed in compositions herein can alternatively or additionally comprise non-volatile silicone oils, which include polyalkyl siloxanes, polyalkylaryl siloxanes and polyethersiloxane copolymers. These can suitably be selected from dimethicone and dimethicone copolyols. Commercially available non-volatile silicone oils include products available under the trademarks Dow Corning 556 and Dow Corning 200 series. Other non volatile silicone oils include that bearing the trademark DC704. Incorporation of at least some non-volatile silicone oil having a high refractive index such as of above 1.5, eg at least 10% by weight (preferably at least 25% to 100% and particularly from 40 to 80%) of the silicone oils is often beneficial in some compositions, because this renders it easier to match the refractive index of the constituents of the composition and thereby easier to produce transparent or translucent formulations.

The water-immiscible liquid carrier may contain from 0% to 100% by weight of one or more liquid silicones. Preferably, there is sufficient liquid silicone to provide at least 10%, better at least 15%, by weight of the whole composition.

Silicon-free hydrophobic liquids can be used instead of, or more preferably in addition to liquid silicones. Silicon-free hydrophobic organic liquids which can be incorporated include liquid aliphatic hydrocarbons such as mineral oils or hydrogenated polyisobutene, often selected to exhibit a low viscosity. Further examples of liquid hydrocarbons are polydecene and paraffins and isoparaffins of at least 10 carbon atoms.

Other suitable hydrophobic carriers comprise liquid aliphatic or aromatic esters. Suitable aliphatic esters contain at least one long chain alkyl group, such as esters derived from $C_1$ to $C_{20}$ alkanols esterified with a $C_8$ to $C_{22}$ alkanoic acid or $C_6$ to $C_{10}$ alkanedioic acid. The alkanol and acid moieties or mixtures thereof are preferably selected such that they each have a melting point of below 20° C. These esters include isopropyl myristate, lauryl myristate, isopropyl palmitate, diisopropyl sebacate and diisopropyl adipate.

Suitable liquid aromatic esters, preferably having a melting point of below 20° C., include fatty alkyl benzoates. Examples of such esters include suitable $C_8$ to $C_{18}$ alkyl benzoates or mixtures thereof, including in particular $C_{12}$ to $C_{15}$ alkyl benzoates eg those available under the trademark Finsolv. Incorporation of such alkyl benzoate esters as at least a fraction of the hydrophobic carrier liquid can be advantageous, because they can raise the average of volatile-silicone-containing carriers, and thereby render it easier to obtain translucent or transparent formulations.

Further instances of suitable hydrophobic carriers comprise liquid aliphatic ethers derived from at least one fatty alcohol, such as myristyl ether derivatives e.g. PPG-3 myristyl ether or lower alkyl ethers of polygylcols such as an ether having named as PPG-14 butyl ether by the CTFA.

Aliphatic alcohols which are liquid at 20° C. may be employed, and it is especially desirable to employ those which are water-immiscible. These include branched chain alcohols of at least 10 carbon atoms such as isostearyl alcohol and octyl dodecanol. Such alcohols can assist in the process of forming a solution of the DOPA derivatives in a water-immiscible carrier liquid during the manufacture of structured gels. Such alcohols can often constitute from at least 10% or 15% by weight of the water-immiscible liquid carrier mixture, in many desirable mixtures comprising up to 70% or 80% of the mixture. In a number of convenient formulations, the proportion of such aliphatic alcohols in said mixture is from 10 or 15% to 30% by weight and in some others, the proportion is greater than 30% by weight.

However, aliphatic alcohols which are solid at 20° C., normally linear alcohols, such as stearyl alcohol are preferably absent or present in no more than 3% by weight of the whole composition, as indicated hereinbefore, since they lead to visible white deposits when a composition is topically applied to skin.

Silicon-free liquids can constitute from 0-100% of the water-immiscible liquid carrier, but it is preferred that silicone oil is present and that the amount of silicon-free constituents preferably constitutes up to 50 or 60% or even up to 80% of water-immiscible carrier liquid and in many instances from 10 to 60% by weight, eg 15 to 30% or 30 to 60% by weight, of the carrier liquid.

Liquid Disperse Phase in Emulsions

If the composition is an emulsion in which the DOPA derivative acts as a structurant in the hydrophobic continuous phase, the emulsion will contain a more polar or lypophobic disperse phase. The disperse phase may be a solution of an active ingredient.

The hydrophilic disperse phase in an emulsion commonly comprises water as solvent and can comprise one or more water soluble or water miscible liquids in addition to or in replacement of water. The proportion of water in an emulsion according to the present invention is often selected in the range of up to 60%, and particularly from 10% up to 40% or 50% of the whole formulation.

One class of water soluble or water-miscible liquids comprises short chain monohydric alcohols, e.g. $C_1$ to $C_4$ and especially ethanol or isopropanol, which can impart a deodorising capability to the formulation. Ethanol gives a cooling effect on application to skin, because it is very volatile. It is preferred that the content of ethanol or any other monohydric alcohol with a vapour pressure above 1.3 kPa (10 mmHg) is not over 15% better not over 8% by weight of the composition.

A further class of hydrophilic liquids comprises diols or polyols preferably having a melting point of below 40° C., or which are water miscible. Examples of water-soluble or water-miscible liquids with at least one free hydroxy group include ethylene glycol, 1,2-propylene glycol, 1,3-butylene glycol, hexylene glycol, diethylene glycol, dipropylene glycol, 2-ethoxyethanol, diethylene glycol monomethylether, triethyleneglycol monomethylether and sorbitol. Especially preferred are propylene glycol and glycerol.

In an emulsion the disperse phase is likely to constitute from 5 to 80 or 85% of the weight of the composition preferably from 5 to 50 or 65% more preferably from 25 or 35% up to 50 or 65%, while the continuous phase with the structurant therein provides the balance from 15 or 35% up to 95% of the weight of the composition. Compositions with high proportion of disperse phase, i.e. from 65 to 85% disperse phase, may be advantageous because they can give good hardness even though the concentration of structurant may be only a small percentage of the total composition.

However, compositions with a lower proportion of disperse phase can also be advantageous because they tend to offer a drier and warmer feel.

An emulsion composition will generally include one or more emulsifying surfactants which may be anionic, cationic, zwitterionic and/or nonionic surfactants. The proportion of emulsifier in the composition is often selected in the range up to 10% by weight and in many instances from 0.1 or 0.25 up to 5% by weight of the composition. Most preferred is an amount from 0.1 or 0.25 up to 3% by weight. Nonionic emulsifiers are frequently classified by HLB value. It is desirable to use an emulsifier or a mixture of emulsifiers with an overall HLB value in a range from 2 to 10 preferably from 3 to 8.

It may be convenient to use a combination of two or more emulsifiers which have different HLB values above and below the desired value. By employing the two emulsifiers together in appropriate ratio, it is readily feasible to attain a weighted average HLB value that promotes the formation of an emulsion.

Many suitable emulsifiers of high HLB are nonionic ester or ether emulsifiers comprising a polyoxyalkylene moiety, especially a polyoxyethylene moiety, often containing from about 2 to 80, and especially 5 to 60 oxyethylene units, and/or contain a polyhydroxy compound such as glycerol or sorbitol or other alditol as hydrophilic moiety. The hydrophilic moiety can contain polyoxypropylene. The emulsifiers additionally contain a hydrophobic alkyl, alkenyl or aralkyl moiety, normally containing from about 8 to 50 carbons and particularly from 10 to 30 carbons. The hydrophobic moiety can be either linear or branched and is often saturated, though it can be unsaturated, and is optionally fluorinated. The hydrophobic moiety can comprise a mixture of chain lengths, for example those deriving from tallow, lard, palm oil, sunflower seed oil or soya bean oil. Such nonionic surfactants can also be derived from a polyhydroxy compound such as glycerol or sorbitol or other alditols. Examples of emulsifiers include ceteareth-10 to -25, ceteth-10-25, steareth-10-25 (i.e. $C_{16}$ to $C_{18}$ alcohols ethoxylated with 10 to 25 ethylene oxide residues) and PEG-15-25 stearate or distearate. Other suitable examples include $C_{10}$-$C_{20}$ fatty acid mono, di or tri-glycerides. Further examples include $C_{18}$-$C_{22}$ fatty alcohol ethers of polyethylene oxides (8 to 12 EO).

Examples of emulsifiers, which typically have a low HLB value, often a value from 2 to 6 are fatty acid mono or possibly diesters of polyhydric alcohols such as glycerol, sorbitol, erythritol or trimethylolpropane. The fatty acyl moiety is often from $C_{14}$ to $C_{22}$ and is saturated in many instances, including cetyl, stearyl, arachidyl and behenyl. Examples include monoglycerides of palmitic or stearic acid, sorbitol mono or diesters of myristic, palmitic or stearic acid, and trimethylolpropane monoesters of stearic acid.

A particularly desirable class of emulsifiers comprises dimethicone copolymers, namely polyoxyalkylene modified dimethylpolysiloxanes. The polyoxyalkylene group is often a polyoxyethylene (POE) or polyoxypropylene (POP) or a copolymer of POE and POP. The copolymers often terminate in $C_1$ to $C_{12}$ alkyl groups.

Suitable emulsifiers and co-emulsifiers are widely available under many trade names and designations including Abil™, Arlacel™, Brij™, Cremophor™, Dehydrol™, Dehymuls™, Emerest™, Lameform™, Pluronic™, Prisorine™, Quest PGPH™, Span™, Tween™, SF1228, DC3225C and Q2-5200.

Cosmetic Actives

The cosmetic actives employable herein can comprise antiperspirant or deodorant actives or pigments.

Antiperspirant Actives

The composition preferably contains an antiperspirant active. Antiperspirant actives, are preferably incorporated in an amount of from 0.5-60%, particularly from 5 to 30% or 40% and especially from 5 or 10% to 30 or 35% of the weight of the composition.

Antiperspirant actives for use herein are often selected from astringent active salts, including in particular aluminium, zirconium and mixed aluminium/zirconium salts, including both inorganic salts, salts with organic anions and complexes. Preferred astringent salts include aluminium, zirconium and aluminium/zirconium halides and halohydrate salts, such as chlorohydrates and activated aluminium chlorohydrates.

Aluminium halohydrates are usually defined by the general formula $Al_2(OH)_xQ_y.wH_2O$ in which Q represents chlorine, bromine or iodine, x is variable from 2 to 5 and x+y=6 while $wH_2O$ represents a variable amount of hydration. Especially effective aluminium halohydrate salts, known as activated aluminium chlorohydrates, are described in EP-A-6739 (Unilever N V et al), the contents of which specification is incorporated herein by reference. Some activated salts do not retain their enhanced activity in the presence of water but are useful in substantially anhydrous formulations, i.e. formulations which do not contain a distinct aqueous phase.

Zirconium actives can usually be represented by the empirical general formula: $ZrO(OH)_{2n-nz}B_z.wH_2O$ in which z is a variable in the range of from 0.9 to 2.0 so that the value 2n-nz is zero or positive, n is the valency of B, and B is selected from the group consisting of chloride, other halide, sulphamate, sulphate and mixtures thereof. Possible hydration to a variable extent is represented by $wH_2O$. Preferable is that B represents chloride and the variable z lies in the range from 1.5 to 1.87. In practice, such zirconium salts are usually not employed by themselves, but as a component of a combined aluminium and zirconium-based antiperspirant.

The above aluminium and zirconium salts may have coordinated and/or bound water in various quantities and/or may be present as polymeric species, mixtures or complexes. In particular, zirconium hydroxy salts often represent a range of salts having various amounts of the hydroxy group. Zirconium aluminium chlorohydrate may be particularly preferred.

Antiperspirant complexes based on the above-mentioned astringent aluminium and/or zirconium salts can be employed. The complex often employs a compound with a carboxylate group, and advantageously this is an amino acid. Examples of suitable amino acids include dl-tryptophan, dl-β-phenylalanine, dl-valine, dl-methionine and β-alanine, and preferably glycine which has the formula $CH_2(NH_2)COOH$.

It is highly desirable to employ complexes of a combination of aluminium halohydrates and zirconium chlorohydrates together with amino acids such as glycine, which are disclosed in U.S. Pat. No. 3,792,068 (Luedders et al). Certain of those Al/Zr complexes are commonly called ZAG in the literature. ZAG actives generally contain aluminium, zirconium and chloride with an Al/Zr ratio in a range from 2 to 10, especially 2 to 6, an Al/Cl ratio from 2.1 to 0.9 and a variable amount of glycine. Actives of this preferred type are available from Westwood, from Summit and from Reheis.

Other actives which may be utilised include astringent titanium salts, for example those described in GB 2299506A.

The proportion of solid antiperspirant salt in a suspension composition normally includes the weight of any water of hydration and any complexing agent that may also be present in the solid active. However, when the active salt is incorporated in solution in a hydrophilic solvent such as a glycol, its weight commonly excludes any water present.

If the composition is in the form of an emulsion the antiperspirant active will be dissolved in the disperse phase. In this case, the antiperspirant active will often provide from 3 to 60% by weight of the disperse phase, particularly from 10% or 20% up to 55% or 60% of that phase. Alternatively, the composition may take the form of a suspension in which antiperspirant active in particulate form is suspended in the water-immiscible liquid carrier. Such a composition will probably not have any separate aqueous phase present and may conveniently be referred to as "substantially anhydrous" although it should be understood that some water may be present bound to the antiperspirant active or as a small amount of solute within the water-immiscible liquid phase. In such compositions, the particle size of the antiperspirant salts often falls within the range of 0.1 to 200 μm with a mean particle size often from 3 to 20 μm. Both larger and smaller mean particle sizes can also be contemplated such as from 20 to 50 μm or 0.1 to 3 μm.

Deodorant Actives

Suitable deodorant actives can comprise deodorant effective concentrations of antiperspirant metal salts, deoperfumes, and/or microbicides, including particularly bactericides, such as chlorinated aromatics, including biguanide derivatives, of which materials known as Igasan DP300™ (triclosan), Tricloban™, and Chlorhexidine warrant specific mention. A yet another class comprises biguanide salts such as are available under the trade mark Cosmosil™. Deodorant actives are commonly employed at a concentration of from 0.1 to 25% by weight.

Optional Ingredients

Other optional ingredients include wash-off agents, often present in an amount of up to 1.0% w/w to assist in the removal of the formulation from skin or clothing. Such wash-off agents are typically nonionic surfactants such as esters or ethers containing a $C_8$ to $C_{22}$ alkyl moiety and a hydrophilic moiety which can comprise a polyoxyalkylene group (POE or POP) and/or a polyol.

A further optional constituent of the formulation comprises one or more further structurants which can be employed in addition to the DOPA derivative. Herein, the DOPAD may be the primary structurant, by which is meant that is employed at a concentration that is higher than that of the further structurant. However, in some advantageous embodiments, the further structurant may be present in an amount that is at least that of the DOPAD. In such advantageous embodiments, the DOPAD is acting to moderate the properties of the further structurant such that the properties using the combined structurant system are superior in at least one desirable respect to using the further structurant alone. The amount of such further structurants in the formulation is often from zero to not more than 15% of the formulation. In some instances, the further structurant is present in a weight ratio to the DOPAD of from 10:1 to 1:10.

The further structurants employable herein can be non-polymeric or polymeric. Solid linear fatty alcohol and/or a wax may be included but are not preferred. In anhydrous compositions notably antiperspirants which are suspension sticks, non-polymeric further structurants, sometimes referred to as gellants, can be selected from fatty acids or salts thereof, such as stearic acid or sodium stearate or 12-hydroxy stearic acid. Linear fatty acids are preferably not used in aqueous sticks, e.g. aqueous emulsion sticks because they can form insoluble precipitates with aluminium ions. Other suitable gellants can comprise dibenzylidene alditols, e.g. dibenzylidene sorbitol. Further suitable gellants can comprise selected N-acyl amino acid derivatives, including ester and amide derivatives, such as N-lauroyl glutamic acid dibutylamide, which gellants can be contemplated in conjunction with 12-hydroxy stearic acid or an ester or amide derivative thereof. Still further gellants include amide derivatives of di or tribasic carboxylic acids, such as alkyl N,N' dialkylsuccinamides, e.g. dodecyl N,N'-dibutylsuccinamide. When employing further structurants comprising N-acyl amino acid derivatives, in some highly desirably formulations their weight ratio to DOPAD is selected in the range of 1:1 to 6:1.

Polymeric structurants which can be employed can comprise organo polysiloxane elastomers such as reaction products of a vinyl terminated polysiloxane and a cross linking agent or alkyl or alkyl polyoxyalkylene-terminated poly (methyl substituted) or poly (phenyl substituted) siloxanes. A number of polyamides have also been disclosed as structurants for hydrophobic liquids. Polymers containing both siloxane and hydrogen bonding groups, which might be used as secondary structurants, have been disclosed in WO 97/36572 and WO 99/06473. If an aqueous disperse phase is present, polyacrylamides, polyacrylates or polyalkylene oxides may be used to structure or thicken this aqueous phase.

It has also been found that invention formulations can include a dibenzylidene alditol, such as dibenzylidene sorbitol, as additional structurant, possibly in conjunction with an N-acyl amino acid derivative. Desirably, the proportion of the alditol in the formulation is selected in the range of from 0.1 to 0.5% by weight. In such formulations, the weight ratio of DOPAD to the alditol, eg dibenzylidene sorbitol, is often selected within the range of 3:1 to 10:1. When an N-acyl amino acid derivative such as GP-1 is also employed, then the weight ratio of DOPAD to alditol is often selected in the range of from about 4:1 to 10:1 and the weight ratio of GP-1 or other amino acid derivative to DOPAD is commonly selected in the range of from about 5:2 to 2:3.

It is highly desirable that any further structurant employed herein is itself fibre-forming, that is to say forms a fibrous structure within the hydrophobic phase. Most preferably the fibre-forming structurant is one in which the fibrous structure is not visible to the human eye.

The compositions herein can incorporate one or more cosmetic adjuncts conventionally contemplatable for cosmetic solids or soft solids. Such cosmetic adjuncts can include skin feel improvers, such as talc or finely divided polyethylene, for example in an amount of up to about 10%; skin benefit agents such as allantoin or lipids, for example in an amount of up to 5%; colours; skin cooling agents other than the already mentioned alcohols, such a menthol and menthol derivatives, often in an amount of up to 2%, all of these percentages being by weight of the composition. A commonly employed adjunct is a perfume, which is normally present at a concentration of from 0 to 4% and in many formulations from 0.25 to 2% by weight of the composition.

Product Form

The sticks produced employing the DOPAD structurants can be either opaque or translucent or even transparent, depending at least partly on the extent to which the refractive indices (RI) of the appropriate ingredients are matched. Translucent or transparent formulations are possible in respect of the invention formulations because the DOPAD structurant forms a fibrous structure within the liquid hydrophobic carrier that is not seen by the human eye. By matched herein is meant that the difference between the refractive indices is less than 0.005 and preferably less than 0.002. In suspension sticks, to achieve at least translucency, it is necessary to match the RI of the suspended cosmetic active, eg the particulate antiperspirant salt, with the RI of the suspending carrier oil mixture. This can be assisted by a suitable choice of oils, and in particular mixtures containing those having an RI of above 1.46, such as from 1.46 to 1.56. In regard to suspended particulates, RI matching can be assisted by two factors. One comprises crushing or grinding the particulates so as to reduce substantially or ideally eliminate hollow spheres which have a different RI, and the second comprises controlling the particle size during the manufacture process or in a subsequent classification process to produce a particle size distribution having no more than a minor fraction in the region of 1 to 10 μM. Matching can be further assisted by modifying the RI of the suspended cosmetic active, such as an aluminium-containing antiperspirant active by post treating it with water (re-hydration) or by retaining a comparatively high water content during the manufacture process. In emulsion formulations, the relevant ingredients to RI match comprise the disperse and continuous liquid phases.

It is highly desirable to employ RI matching as indicated above in conjunction with the exclusion, to the extent necessary, of additional suspended materials having a different refractive index from the suspending medium, such as for example a suspended filler or additional cosmetic active, to enable the resultant composition to transmit at least 1% light (in the test described hereinafter).

Mechanical Properties and Product Packages

The compositions of this invention are structured liquids and are firm in appearance. A composition of this invention will usually be marketed as a product comprising a container with a quantity of the composition therein, where the container has an aperture for the delivery of composition, and means for urging the composition in the container towards the delivery aperture. Conventional containers take the form of a barrel of oval cross section with the delivery aperture at one end of the barrel.

A composition of this invention may be sufficiently rigid that it is not apparently deformable by hand pressure and is suitable for use as a stick product in which a quantity of the composition in the form of a stick is accommodated within a container barrel having an open end at which an end portion of the stick of composition is exposed for use. The opposite end of the barrel is often closed.

Generally the container will include a cap for its open end and a component part which is sometimes referred to as an elevator or piston fitting within the barrel and capable of relative axial movement along it. The stick of composition is accommodated in the barrel between the piston and the open end of the barrel. The piston is used to urge the stick of composition along the barrel. The piston and stick of composition may be moved axially along the barrel by manual pressure on the underside of the piston using a finger or rod inserted within the barrel. Another possibility is that a rod attached to the piston projects through a slot or slots in the barrel and is used to move the piston and stick. Preferably the container also includes a transport mechanism for moving the piston comprising a threaded rod which extends axially into the stick through a correspondingly threaded aperture in the piston, and means mounted on the barrel for rotating the rod. Conveniently the rod is rotated by means of a hand-wheel mounted on the barrel at its closed end, i.e. the opposite end to the delivery opening.

The component parts of such containers are often made from thermoplastic materials, for example polypropylene or polyethylene. Descriptions of suitable containers, some of which include further features, are found in U.S. Pat. Nos. 4,865,231, 5,000,356 and 5,573,341.

Composition Preparation

Compositions of this invention can be produced by conventional processes for making cosmetic solids. Such processes involve forming a heated mixture of the composition at a temperature which is sufficiently elevated that all the structurant dissolves, pouring that mixture into a mould, which may take the form of a dispensing container, and then cooling the mixture whereupon the structurant solidifies into a network of fibres extending through the water-immiscible liquid phase.

A convenient process sequence for a composition which is a suspension comprises first forming a solution of the structurant in the water-immiscible liquid or one of the water-immiscible liquids. This is normally carried out by agitating the mixture at a temperature sufficiently high that all the structurant dissolves (the dissolution temperature) such as a temperature in a range from 50 to 140° C. Thereafter, the particulate constituent, for example particulate antiperspirant active, is blended with the hot mixture. This must be done slowly, or the particulate solid must be preheated, in order to avoid premature gelation. The resulting blend is then introduced into a dispensing container such as a stick barrel. This is usually carried out at a temperature 5 to 30° C. above the setting temperature of the composition. The container and contents are then cooled to ambient temperature. Cooling may be brought about by nothing more than allowing the container and contents to cool. Cooling may be assisted by blowing ambient or even refrigerated air over the containers and their contents.

In a suitable procedure for making emulsion formulations, a solution of the structurant in the water-immiscible liquid phase is prepared at an elevated temperature just as for suspension sticks. If any emulsifier is being used, this is conveniently mixed into this liquid phase. Separately an aqueous or hydrophilic disperse phase is prepared by introduction of antiperspirant active into the liquid part of that phase (if this is necessary: antiperspirant actives can sometime be supplied in aqueous solution which can be utilised as is). If possible, this solution of antiperspirant active which will become the disperse phase is preferably heated to a temperature similar to that of the continuous phase with structurant therein, but without exceeding the boiling point of the solution, and then mixed with the continuous phase. Alternatively, the solution is introduced at a rate which maintains the temperature of the mixture. If it is necessary to work at a temperature above the boiling temperature of the disperse phase, or at a temperature where evaporation from this phase is significant, a pressurised apparatus could be used to allow a higher temperature to be reached. With the structurant materials of this invention this is usually unnecessary. After the two phases are mixed, the resulting mixture is filled into dispensing containers, typically at a temperature 5 to 30° C. above the setting temperature of the composition, and allowed to cool as described above for suspension sticks.

Many of the cosmetic composition according to the present invention employ a mixture of hydrophobic carrier fluids. In some convenient preparative routes, it is desirable to dissolve the DOPAD structurant in a liquid component of the composition, such as an alcohol, eg an alcoholic carrier fluid, ie, a branched aliphatic alcohol, eg isostearyl alcohol or octyldodecanol, optionally in conjunction with an alcohol having some water-miscibility and boiling point above the dissolution temperature of DOPAD in the alcoholic fluid. This enables the remainder of the carrier fluids to avoid being taken to the temperature at which the DOPA dissolves or melts. The proportion of the carrier fluids for dissolving the DOPA is often from 15 to 65% by weight of the carrier fluids, and particularly from 20 to 40%.

Structurant Preparation

The DOPA derivatives employed as structurants herein can be made by esterifying DOPA in acid form with the alcohol corresponding to the residue desired in the DOPA derivative.

In one convenient precursor step, the DOPA acid (DOPAA) can be made by cyclising aspartame, preferably in the presence of a substantial excess of a low molecular weight aliphatic alcohol, such as isopropanol, under reflux for a long period. Desirably, the alcohol is employed in a weight ratio to aspartame of greater than 50:1 such as up to 100:1, and the reaction is continued for at least 10 hours at reflux temperature, such as from 15 to 24 hours. During the reaction, the aspartame gradually dissolves. On cooling, the resultant solution yields a white powder. Removal of the solvent from the filtrate yields a solid which, after washing with acetone, provides a further amount of the white product, confirmed by a combined yield of the DOPA acid of 79%.

DOPAA can be reacted with the relevant alcohol of formula $R_4OH$, preferably in a mole ratio to the DOPAA of at least 1:1 to 10:1, particularly from 1.5:1 to 7:1 and especially at least 2:1 in dimethyl sulphoxide, conveniently in a ratio of at least 4:1 (vol:wt), preferably from 6:1 to 12:1, and preferably in the presence of a promoter, such as a carbonyldiimidazole, in an amount preferably from 0.5 to 2 moles of promoter per mole of DOPA acid. The reaction is conveniently carried out at a mildly elevated temperature, such as up to 60° C. and particularly from 40 to 60° C. for a period of at least 6 hours and preferably from 9 to 24 hours. The resultant solution is quenched in excess ambient or cooler water, desirably after the solution has cooled to ambient, a solid precipitates and is filtered off, water washed until no residual diimidazole remained and then can be purified by washing with diethyl ether or toluene, and dried.

EXAMPLES

Example 1 and Comparisons CA to CI

Preparation of Structurants

These Examples and Comparisons were carried out by the following general method employing (2S-cis)-(−)-5-benzyl-3,6-dioxo-2-piperazine acetic acid (DOPAA) which was reacted with the alcohols and the amounts of reagents and promoter specified in Table 1 below.

A 250 ml 3 necked round bottomed flask equipped with a stirrer was charged with (2S-cis)-(−)-5-benzyl-3,6-dioxo-2-piperazine acetic acid (DOPAA), and methyl sulfoxide (8 mls per 1 g of DOPAA) was then introduced at laboratory ambient temperature (about 22° C.) with stirring. The DOPAA dissolved only partially. 1,1'-carbonyldiimidazole was then introduced with stirring in the amount specified in the Table. Vigorous effervescence occurred and the reaction mixture was left stirring at room temperature for 45 minutes after which time the reaction mixture went clear. The specified alcohol was stirred into the clear reaction mixture and maintained at 50° C. overnight (between 16 and 20 hours), whereupon it was allowed to cool to ambient temperature (about 22° C.), and poured into water, producing a precipitate which was filtered off and washed with further quantities of water until any residual diimidazole had been removed (as shown by $^1$Hnmr). The washed precipitate was then washed with diethyl ether, except for CB which was washed with toluene. The washed product was dried in a vacuum oven to constant weight and its melting point determined, the results quoted herein being obtained by DSC with a heating rate of 10° C./min, except for those marked$^{ET}$, which were obtained using a an Electrothermal 9109 digital melting point measuring apparatus. The purity of certain of the products could be determined by the selected HPLC method, because such derivatives were not elutable.

The DOPAD materials in Examples 1.16 to 1.18 were produced on a smaller scale using a modified reaction method in which the DOPAA was activated with CDI in a single reaction vessel in 125 ml DMSO solution. Once activated, this was transferred by volume to a reaction tube in a Radleys'™ 12 place reaction carousel containing the appropriate amount of the chosen alcohol.

The purity of DOPAD materials Ex1.1 to Ex 1.19 and CA to CK was measured by reverse phase HPLC with ultraviolet (UV) detection.

A mobile phase was made comprising 300 ml aliquot of deionised water, to which was added a 700 ml aliquot of HPLC grade acetonitrile and 1.0 ml of trifluoroacetic acid (Aldrich spectrophotometric grade, TFA) and mixed thoroughly. 0.001 g of CDP sample was weighed into a 2 ml HPLC vial and made up to volume with the mobile phase.

The sample was then analysed in a Hewlett Packard HPLC analyser equipped with a Hypersil ODS™ 5 µm $C_{18}$, 250×4.6 mm @ Room Temp column, a Hewlett-Packard 1050 Series Autosampler and Hewlett-Packard 1050 UV Diode Array @ 210 nm Detector. The analysis was carried under the following conditions:

TABLE 1

| Isocratic/gradient | | Isocratic | | | | | |
|---|---|---|---|---|---|---|---|
| Flow rate | | 1.2 ml/minute | | | | | |
| Run time | | 5 minutes | | | | | |
| Temperature | | Ambient | | | | | |
| Injection volume | | 20 µl | | | | | |
| Ex or | Alcohol | CDI | DOPA | Yield | | Purity | MP |
| Comp | | mmol | mmol | mmol | g | % | % | ° C. |
| 1.1 | (1s,2R,5S)-(+)-Menthol | 18 | 4.0 | 3.68 | 0.75 | 49 | 98.7 | 238 |
| 1.2 | Thymol | 73.6 | 16.2 | 14.7 | 3.3 | 56 | 99.3 | 212 |
| 1.3 | Menthol (racemic) | 73.6 | 16.2 | 14.7 | 1.0 | 17 | 48.4 | 216 |

TABLE 1-continued

| | | | | | | | | |
|---|---|---|---|---|---|---|---|---|
| 1.4 | 3,5-dimethyl-cyclohexanol | 92 | 22 | 18.4 | 1.5 | 21 | 94 | 212 |
| 1.5 | 2,2,6,6-tetramethyl-4-piperidinol | 92 | 22 | 18.4 | 1.2 | 16 | 97.8 | 225 |
| 1.6 | 1R,2R,3R,5S-(−)-iso-pinocamphenol | 92 | 22 | 18.4 | 4.16 | 55 | 68 | >200 |
| 1.7 | Nonylphenol | 92 | 22 | 18.4 | 4.07 | 46 | 83.6 | 191 |
| 1.8 | (1R,2S,5S)-(−)-Menthol | 92 | 22 | 18.4 | 7.72 | 51 | 85.9 | 233 |
| 1.9 | 4-t-butyl phenol | 95.3 | 22.9 | 19.1 | 7.13 | 94.6 | 99.1 | 237 |
| 1.10 | 4-t-amyl phenol | 95.3 | 22.9 | 19.1 | 6.86 | 87.9 | 100 | 211 |
| 1.11 | 4-isopropyl phenol | 66.3 | 26.5 | 22.9 | 7.31 | 83.8 | 99.4 | >230 |
| 1.12 | 3,5-dimethyl phenol | 66.3 | 26.5 | 22.9 | 6.95 | 83.7 | 99.6 | >200 |
| 1.13 | butyl-4-hydroxy benzoate | 95.4 | 22.9 | 19.1 | 6.96 | 83.1 | 98.5 | 217 |
| 1.14 | Carveol | 95.3 | 22.9 | 19.1 | 4.22 | 55.7 | 95.0 | 215$^{ET}$ |
| 1.15 | Carvacrol | 95.3 | 22.9 | 19.1 | 6.62 | 87.9 | 99.1 | 229$^{ET}$ |
| 1.16 | 5,6,7,8-tetra-hydro napth-2-ol | 18.4 | 4.6 | 3.8 | 1.14 | 76.5 | 99.3 | 220$^{ET}$ |
| 1.17 | decahydro napth-2-ol | 19.0 | 4.6 | 3.8 | 0.27 | 17.8 | 69.7 | 189$^{ET}$ |
| 1.18 | 2-isopropoxy-phenol | 19.0 | 4.6 | 3.8 | 0.57 | 37.8 | 98.8 | 178$^{ET}$ |
| 1.19 | Phenol | 147.4 | 35.4 | 30.5 | 8.95 | 87.9 | 99.7 | 246 |
| CA | 2-ethyl-butanol | 165.5 | 36.4 | 33.0 | 7.82 | 70 | 94.5 | 174 |
| CB | 3,5,5-tri-methylhexanol | 114.5 | 25.0 | 22.9 | 6.51 | 71 | 100 | 121 |
| CC | Oleyl alcohol | 92 | 20 | 18.4 | 5.15 | 67 | cnd | 143 |
| CD | Cyclohexyl-methanol | 92 | 22 | 18.4 | 2.04 | 30 | 98.4 | 187 |
| CE | Cholesterol | 121.2 | 36.3 | 24.2 | 3.23 | 35 | 100 | >210 |
| CF | Norbonane-menthol | 92 | 22 | 18.4 | 4.95 | 68 | 100 | 201 |
| CG | (1R)-(−)-Myrentol | 92 | 22 | 18.4 | 7.11 | 65 | 99.4 | 160 |
| CH | Cyclohexanol | 147.4 | 35.4 | 30.5 | 2.12 | 20.4 | 91.4 | 224 |
| CI | n-dodecanol | 95.0 | 22.8 | 19.1 | 6.8 | 80 | 99.3 | 182$^{ET}$ |
| CJ | n-octadecanol | 95.3 | 22.8 | 19.1 | 5.11 | 52 | cnd | 175$^{ET}$ |
| CK | benzyl alcohol | 95.2 | 22.8 | 19.1 | 5.8 | 87 | 99.7 | 222$^{ET}$ |

Materials

The materials used in gel studies or the preparation of cosmetic formulations, and their proprietary names, other than the products of Example 1, were as follows:
1) Isostearyl alcohol (ISA) (Pricerine 3515™-Uniqema)
2) $C_{12-15}$ alkyl benzoate (Finsolv TN™ from Finetex Inc)
3) Octyl dodecanol (Eutanol G™-Cognis)
4) Volatile cyclomethicone (DC 245™-Dow Corning Inc)
5) Hydogenated Polydecene (Silkflo 364 NF™-Albemarle)
6) 1,1,5,5-tetraphenyl trisiloxane (DC704™: Dow Corning Inc)
7) N-lauroyl-L-glutamic acid Di-n-butylamide (GP-1™-Ajinomoto Co Inc)
8) Dimethicone Copolyol (Abil EM90™-Th. Goldschmidt A G)
9) Al/Zr Tetrachlorohydrex glycine complex (Reach 908™-Reheis Inc)
10) Milled Macrospherical AACH (A418™-Summit)
11) 50% aqueous solution of Al/Zr pentachlorohydrate (Zirconal 50™-B K Giulini)
12) Water-modified AZAG, made in house by freeze drying a solution of AZAG (Rezal 67™) and sieving to obtain particulate solid free from hollow particles (~37% of particles <10 μm) and water treated to RI=1.526.
13) PG5—Al/Zr pentachlorohydrex glycine complex (B K Giulini) free from hollow particles (~25% particles <10 μM) (RI=1.530)
14) BMA—Benzyl alcohol-Acros
15) DBS—Dibenzylidene sorbitol (Roquette Corp)
16) 12-HSA—12-hydroxystearic acid (CasChem Inc)
17) Rezal 36 GP (solid Al/Zr tetrahydrochlorex glycine salt from Reheis Inc)
18) Reach 908 (solid Al/Zr tetrahydrochlorex glycine salt from Reheis Inc)
19) Versamid 930-polyamide from Cognis
20) DDK H18, Silica from Wacker-Chemie GmbH
21) HDD H30, silica from Wacker-Chemie GmbH
22) HDD H30RX, silica from Wacker-Chemie GmbH
23) tri(1,2-propanediol) n-butyl ether (Dowanol TPNB™ from Dow Corning Inc
24) propane-1,2-diol from Fisher
25) di (propane-1,2-diol) from Acros
26) PEG-30 dipolyhydroxystearate (Arlacel P135™ from Uniqema Example 2

Structured Gels

In this Example, gels were made or attempted to be made in a number of representative organic solvents, having the refractive index shown in Table 2 below, using the structurants produced in Example 1 or the comparisons.

The gels were prepared in 30 ml clear glass bottles. The solvent and gelling agent were weighed directly into the bottle to give a total mixture weight of log. A small Teflon stirrer bar was placed in the bottle and the mixture stirred and heated until the cyclo dipeptide had dissolved. The bottle was then removed from the heat and the solution allowed to cool and gel under quiescent conditions.

The gel hardness was determined by a skilled assessor of gels using a qualitative assessment by comparison with standard gels after the gels had been stored at ambient temperature for 1 day or 3 days if over a week-end. The clarity was determined by visual assessment by comparison with standards and for some samples, light transmission measurements were made by the general method described in WO 00/61082, incorporated herein by reference. The results are summarised herein in Table 4.

Gel stability was assessed of a number of samples employing the structurant at a concentration of 1.5% by weight by storing them for a long period at ambient temperature (20 to 25° C.) and observing the change, if any in their appearance or properties after the stated length of time, which time month. The results are summarised in Table 5.

TABLE 2

| Solvent | RI |
|---|---|
| ISA | 1.4559 |
| Finsolv TN | 1.4841 |

TABLE 2-continued

| Solvent | RI |
|---|---|
| Eutanol G | 1.4538 |
| 50:50 ISA: DC245 | 1.4278 |
| 50:50 ISA: Finsolv TN | 1.4700 |
| 50:50 ISA: Silkflo 364NF | 1.4552 |
| 50:50 ISA: DC704 | 1.5059 |

TABLE 3

| Transparency | | Hardness of gel | | Descriptor | |
|---|---|---|---|---|---|
| O | opaque | 0 | Very soft | G | Gel |
| t | Translucent | 1 | Soft | U | Undissolved Solids |
| T | Transparent | 2 | Soft/Medium | P | Paste |
| * | % light | 3 | Medium | L | Liquids present |
| | transmitted | 4 | Medium/Hard | D | Did not dissolve |
| | | 5 | Hard | nd | not determined |
| | | r | Rubbery | | |

TABLE 4

| Product of | Ex 1.1 | | CA | | Ex 1.2 | |
|---|---|---|---|---|---|---|
| Liquid Carrier | wt % | Result | wt % | Result | wt % | Result |
| ISA | 1.5 | t, 3, G | 1.5 | T, 3, G | 1.5 | T, 5, G |
|  | 2.5 | t, 5, G | 2.5 | t, 5, G | | |
|  | 5.0 | t, 5, G | | | | |
| Finsolv TN | 2.5 | T, 3, G | 2.5 | t, 5, G | | |
| Eutanol G | 2.5 | t, 3, G | 2.5 | t, 3, G | | |
| 50:50 ISA: DC245 | 1.0 | t, 2, G | 1.0 | t, 2, G | 1.5 | T, 5, G |
|  | 1.5 | t, 3, G | 1.5 | t, 3, G | | |
| 50:50 ISA: Finsolv TN | 1.5 | T*93, 3, G | 1.5 | t, 3, G | 1.5 | T*83, 5, G |
|  | 2.5 | t, 5, G | 2.5 | t, 5, G | | |
| 50:50 ISA Silkflo 364NF | 1.5 | t, 4, G | 1.5 | t, 3, G | 1.5 | T*81, 5, G |
| 50:50 ISA: DC704 | 1.5 | T*91, 5, G | | | 1.5 | T, 5, G |

| Product of | Ex 1.3 | | Ex 1.4 | | Ex 1.5 | |
|---|---|---|---|---|---|---|
| Liquid Carrier | wt % | Result | wt % | Result | wt % | Result |
| ISA | 1.5 | t, 1, G | 1.5 | T,3,G | 1.5 | T, r, G + U |
| 50:50 ISA: DC245 | 1.5 | t, 1, G + U | 1.5 | T, 3, G + U | 1.5 | T, r, G + U |
| 50:50 ISA: Finsolv TN | 1.5 | t, 1, G + U | 1.5 | T*B4, 3, G | 1.5 | T, r, G + U |
| 50:50 ISA: Silkflo 364NF | 1.5 | t, 1, G + U | 1.5 | T, 3, G | 1.5 | T, r, G + U |

| Product of | Ex 1.6 | | Ex 1.7 | | Ex 1.8 | |
|---|---|---|---|---|---|---|
| Liquid Carrier | wt % | Result | wt % | Result | wt % | Result |
| ISA | 1.5 | T, 3, G | 1.5 | T, 3, G | 1.5 | T, 3, G |
| 50:50 ISA: DC245 | 1.5 | t, 2, G + U | 1.5 | O, 3, G | 1.5 | U + L |
| 50:50 ISA: Finsolv TN | 1.5 | T*68, 3, G | 1.5 | t/O, 3, G | 1.5 | T, 3, G |
| 50:50 ISA: Silkflo 364NF | 1.5 | t, 1, G | 1.5 | O, 3, G | 1.5 | t, 3, G |

TABLE 4-continued

| Product of | Ex 1.9 | | Ex 1.10 | | Ex 1.11 | |
|---|---|---|---|---|---|---|
| Liquid Carrier | wt % | Result | wt % | Result | wt % | Result |
| ISA | 1.5 | T, 3, G | 1.5 | t, 3, G | 1.5 | T, 3, G |
| 50:50 ISA: DC704 | 1.5 | t, 3, G | 1.5 | T, 3, G | | |
| 25:75 ISA: DC704 | 1.5 | T, 3, G | 1.5 | T, 3, G | | |

| Product of | Ex 1.12 | | Ex 1.13 | | Ex 1.14 | |
|---|---|---|---|---|---|---|
| Liquid Carrier | wt % | Result | wt % | Result | wt % | Result |
| ISA 25:75 ISA: DC704 | 1.5 | T, 3, G | 1.5 | t, 3, G | 1.5 | T, 5, G |
| 50:50 ISA: Finsolv TN | | | 1.5 | t, 3, G | 1.5 | T, 4, G |
| | | | | | 1.5 | t, 3, G |

| Product of | Ex 1.15 | | Ex 1.16 | | Ex 1.17 | |
|---|---|---|---|---|---|---|
| Liquid Carrier | wt % | Result | wt % | Result | wt % | Result |
| ISA 25:75 ISA: DC704 50:50 ISA: Finsolv TN | 1.5 | t, 3, G<br>T, 4, G<br>t, 3, G | 1.5 | t, 3, G | 1.5<br>1.5 | T, 3, G<br>T, 3, G |

| Product of | Ex 1.18 | |
|---|---|---|
| Liquid Carrier | wt % | Result |
| ISA | 1.5 | t, 3, G |
| 25:75 ISA: DC704 | 1.5 | T, 2, G |
| 50:50 ISA: Finsolv TN | 1.5 | T, 3, G |

| Product of | CB | | CC | | CD | |
|---|---|---|---|---|---|---|
| Liquid Carrier | wt % | Result | wt % | Result | wt % | Result |
| ISA | 1.5 | t, 2, G | 1.5 | O, Or, G | 1.5 | O, P |
| 50:50 ISA: DC245 | 1.5 | t, 3, G | 1.5 | T, 1, G (leaky) | 1.5 | U + L |
| 50:50 ISA: Finsolv TN | 1.5 | t, 1, G | 1.5 | T, 1r, G | 1.5 | O, P |
| 50:50 ISA: Silkflo 364NF | 1.5 | t, 2, G | 1.5 | T, 1r, G | 1.5 | O, P |

| Product of | CE | | CF | | CG | |
|---|---|---|---|---|---|---|
| Liquid Carrier | wt % | Result | wt % | Result | wt % | Result |
| ISA | 1.5 | U + L | 1.5 | O, P | 1.5 | O, P |
| 50:50 ISA: DC245 | 1.5 | U + L | 1.5 | U + S | 1.5 | O, P |
| 50:50 ISA: Finsolv TN | 1.5 | U + L | 1.5 | O,P | 1.5 | O, P |
| 50:50 ISA: Silkflo 364NF | 1.5 | U + L | 1.5 | U + S | 1.5 | O, P |

| Product of | CI | | CJ | | CK | |
|---|---|---|---|---|---|---|
| Liquid Carrier | wt % | Result | wt % | Result | wt % | Result |
| ISA | 1.5 | L + O, P | 1.5 | O, P | 1.5 | O, P |
| 50:50 ISA: DC704 | 1.5 | O, 0, g | 1.5 | O,P | 1.5 | O, P |

It will be recognised from the foregoing that the comparison gelators, a number of which have been praised in the prior art, are manifestly inferior to the gelators employed in the instant invention.

TABLE 5

| Product of | Initial Gel Description | Gel Description after Storage at Room Temperature |
| --- | --- | --- |
| Ex 1.1 | transparent, medium gels | unchanged after 12 months |
| Ex 1.2 | transparent, hard gels | unchanged after 12 months |
| Ex 1.3 | transparent, soft gels + undissolved solid | unchanged after 12 months |
| Ex 1.4 | transparent, medium gels | unchanged after 12 months |
| Ex 1.5 | transparent, soft, rubbery gels + undissolved solid | DC245/Finsolv mixture initially started to turn opaque and leak solvent after 1 day, but did not deteriorate after 8 months. |
| Ex 1.6 | translucent, soft/medium gels | unchanged after 12 months |
| Ex 1.7 | transparent/opaque medium gels | slight loss of clarity after 3 months, but no further change in next 9 months. |
| Ex 1.8 | transparent medium gels. No gel with DC245 mixture. | unchanged after 8 months) |
| Ex 1.9 | transparent medium gels | unchanged after 6 months |
| Ex 1.10 | transparent/translucent medium gels | unchanged after 6 months |
| Ex 1.11 | transparent medium gel | unchanged after 6 months |
| Ex 1.12 | transparent hard gel | unchanged after 6 months |
| Ex 1.13 | translucent medium gels | unchanged after 6 months |
| Ex 1.14 | transparent medium/hard gels | unchanged after 3 months |
| Ex 1.15 | translucent medium gels | unchanged after 3 months |
| Ex 1.16 | translucent medium gel | unchanged after 2 months (will update) |
| Ex 1.17 | transparent medium gel | unchanged after 2 months (will update) |
| Ex 1.18 | transparent medium gel | unchanged after 1 month (will update) |
| Ex 1.19 | transparent medium or medium hard gel | unchanged after at least 7 months |
| CA | transparent/translucent, soft/medium gels | gels were unsuitable to make sticks because they became very soft and opaque within 2 weeks and leaky within 4 to 6 weeks |
| CB | translucent, soft/medium gels | gels were unsuitable to make sticks because they became very soft and opaque within 2 weeks and leaky within 4 to 6 weeks |
| CC | translucent, soft, rubbery gels | gels were unsuitable to make sticks because they became opaque and collapsed within 1 day |
| CD | opaque pastes or white precipitates in clear solution | not a gel |
| CE | no gels | not a gel |
| CF | did not dissolve or precipitated as opaque crystalline slush | not a gel |
| CG | opaque pastes | not a gel |
| CH | translucent medium or medium/soft gel | gel became opaque, often within days and collapsed within 1 to 6 weeks |

From Table 4, it can be seen than the invention structurants were able to produce gels in a wide range of representative hydrophobic liquid carrier systems, whereas various related structurants in RA did not satisfy the criteria of the instant invention were not so able. Some comparative structurants produced opaque pastes or simply produced a mixture of undissolved solids plus supernatant liquid.

From Table 5, it can be seen that even those structurants which produced gels initially, such as CA, CB and CC, exhibited poor stability, becoming opaque and soft, followed by leaking, and/or collapsed quickly, whereas those gels produced using structurants according to the present invention were considerably more stable. Many of the invention gels were not showing any discernible change after several months. It will further more be recognised that the invention gellants employing $R_A$ that is unsaturated in the ring or a ring that is substituted by an alkyl ether or ester group is superior to a comparison DOPAD in which RA represents cyclohexyl. Likewise, it can be seen that the invention DOPADs in which the ring is a direct substituent of the cyclic dipeptide are superior to comparisons in which an unsaturated (phenyl) ring is separated from the cyclic dipeptide by an intervening methylene group.

Examples 3 to 6

Cosmetic Stick Formulations

A number of cosmetic stick compositions were prepared, containing the ingredients specified in Tables 6 and 8 to 10 below. Their properties were measured by the methods described hereinafter and at the times indicated in the summaries.

Example 3

Opaque Suspension Sticks

In Example 3, opaque sticks were made by dissolving the specified cyclo dipeptide structurant in the liquid alcohol or alcohol mixture, eg isostearyl alcohol whilst with heated and stirring using an overhead paddle stirrer until complete dissolution had occurred. In formulations additionally containing a further structurant, namely GP1 DBS and/or 12-HSA, the latter was dissolved into solution of the cyclo dipeptide structurant at a temperature of about 5 to 10° C. lower. The remaining carrier oils were heated to approximately 50° C. and stirred using a stirrer bar and the desired solid antiperspirant active was introduced slowly and with gentle stirring into them. When all the active had been added, the mixture was sheared using a Silverson mixer at 7000 rpm for 5 minutes to ensure the active was fully dispersed. The active/oil mixture was then heated in an oven to 85° C. and mixed into the structurant solution which had been allowed to cool to 90° C. The temperature of the stirred mixture was kept at 85° C. until it was poured into conventional commercial 50 g stick barrels and allowed to cool except for formulations containing GP1 which were poured at approximately 75° C.

The formulations and properties of the sticks are summarised in Table 6 below.

TABLE 6

| Ingredient | Ex 3.1 | Ex 3.2 | Ex 3.3 | Ex 3.4 | Ex 3.5 |
|---|---|---|---|---|---|
| | | | % by weight | | |
| Ex 1.2 Product | 2.5 | 2.5 | 1.5 | 1 | |
| Ex 1.6 Product | | | | 1.5 | |
| GP1 | | | 2.5 | 3.0 | 2.5 |
| Prisorine 3515 | 35.75 | 35.75 | 30 | 28.2 | 30 |
| Finsolv TN | 35.75 | | | 20.9 | |
| DC704 | | 35.75 | 40 | | 40 |
| DC245 | | | | 20.9 | |
| Reach 908 | 26.0 | 26.0 | 26.0 | 26.0 | 26.0 |
| | | | Properties | | |
| Hardness (mm) | 16.5 | 15.2 | 13.8 | 18.6 | 14.3 |
| pay-off (g) at $t_o$ on WetorDry | 0.35 | 0.25 | 0.31 | 0.27 | 0.3 |
| whiteness t = 24 hr on WetorDry | 13 | 16 | 14 | 27 | 20 |
| pay-off (g) at $t_o$ on wool | 0.99 | 0.63 | 0.82 | 0.63 | 1.08 |
| whiteness t = 24 hr on wool | 17 | 17 | 16 | 15 | 20 |

Comparative data for a commercial suspension stick structured using GP1 (GS) and a commercial wax-structured suspension stick (WS) is given in Table 7 below.

TABLE 7

| Comparison | GS | WS |
|---|---|---|
| Hardness (mm) | 11.3 | 10.3 |
| pay-off (g) at $t_o$ on WetorDry | 0.40 | 0.39 |
| whiteness t = 24 hr on WetorDry | 28 | 121 |
| pay-off (g) at $t_o$ on wool | 0.61 | 1.10 |
| whiteness t = 24 hr on wool | 23 | 110 |

From Table 7, it can be seen that sticks of acceptable firmness can be obtained using the invention structurants at comparatively low concentrations of the structurant. Moreover, even though suspension sticks that are structured using the invention structurants are a little softer (as measured by a penetrometer) than either the GS or WS sticks and therefore might be expected to suffer from a higher pay-off and higher visible deposits, the pay-off is similar to such sticks and the whiteness is, on balance, lower.

Example 4

Transparent Suspension Sticks

The sticks in this Example were made using the process of Example 3 together with a preparatory step. In the preparatory step, the RI of the antiperspirant active was first measured using a standard procedure (Becke line test). The proportions of each of the carrier oils were then determined (through calculation and measurement) such that their weight averaged refractive index was closely matched to that of the active. The formulations are summarised in Table 8 below.

TABLE 8

| Ingredient | 4.1 | 4.2 | 4.3 | 4.4 | 4.5 | 4.6 | 4.7 | 4 comp |
|---|---|---|---|---|---|---|---|---|
| | | | | % by weight | | | | |
| Ex 1.2 | 1.51 | 1.5 | 1.5 | | | | 1.0 | |
| Ex 1.4 | | | | 0.70 | | | | |
| Ex 1.7 | | | | | 1.5 | | | |
| Ex 1.1 | | | | | 1.0 | | | |
| GP-1 | | 3.0 | 4.0 | 4.05 | | 4.0 | 3.0 | 5.0 |
| ISA | 18.34 | 17.61 | 17.36 | 17.55 | 17.61 | 17.36 | 16.71 | 17.49 |
| DC704 | 55.03 | 52.89 | 52.14 | 52.7 | 52.89 | 52.14 | 54.29 | 52.51 |
| A418 | 25.12 | 25.0 | 25.0 | 25.0 | 25.0 | 25.0 | | 25.0 |
| AZAG H2 | | | | | | | 25.0 | |
| | | | | Properties | | | | |
| Hardness (mm) | 23 | 14.7 | 13.1 | 16.1 | 14.8 | n/d | 16.2 | 15.9 |
| Clarity (% T) | 44 | 12.7 | 15.4 | 12.0 | 9.9 | 1.6% | 0.7 | 5.9 |
| Visual Score | 8 | 2 | 1 | 3 | 0 | <-12 | <-12 | -2 |
| pay-off (g) at $t_o$ on wool | nd | 0.88 | 0.54 | 0.92 | 0.58 | n/d | 0.83 | 0.97 |
| whiteness t = 24 hr on wool | nd | 15 | 17 | 20 | 17 | n/d | 17 | 13 |

| Ingredients | 4.8 | 4.9 | 4.10 | 4.11 | 4.12 | 4.13 |
|---|---|---|---|---|---|---|
| | | | % by weight | | | |
| Ex1.2 | 2.81 | | 1.5 | 1.7 | 1.5 | 1.5 |
| Ex1.9 | | 3.0 | | | | |
| GP-1 | | | 2.0 | | | 4.0 |
| DBS | | | 0.25 | 0.4 | | |
| 12-HSA | | | | | 5.0 | |
| ISA | 8.81 | | 17.8 | 18.46 | 15.51 | 15.735 |
| DC704 | 42.36 | 29.47 | 53.45 | 52.48 | 52.99 | 53.765 |
| Benzyl Alcohol | 8.81 | 19.68 | | 1.96 | | |
| Finsolv TN | 12.21 | 22.83 | | | | |
| A418 | 25.0 | 25.0 | 25.0 | 25.0 | 25.0 | |
| P5G | | | | | | 25.0 |
| | | | Properties | | | |
| Hardness (mm) | 14.0 | 20.1 | 13.5 | 17.2 | 13.3 | 12.1 |
| Clarity (% T) | 23.0 | 6.1 | 19.4 | 15.3 | 12.2 | 2.2 |
| Clarity (visual score) | n/d | n/d | 2 | 3 | 0 | -9 |

| Ingredients | 4.14 | 4.15 | 4.16 | 4.17 | 4.18 |
|---|---|---|---|---|---|
| | | | % by weight | | |
| Ex1.2 | 1.7 | 2.0 | | | |
| Ex1.14 | | | 1.0 | | |
| Ex1.15 | | | | 0.7 | |
| Ex1.16 | | | | | 0.4 |
| GP-1 | 2.0 | 2.0 | 4.0 | 4.0 | 4.0 |
| ISA | 16.14 | 17.98 | 15.848 | 15.916 | 15.32 |
| DC704 | 55.16 | 51.1 | 54.152 | 54.384 | 53.30 |
| Benzyl Alcohol | | 1.92 | | | 1.98 |
| A418 | | 25.0 | 125.0 | 25.0 | 25.0 |
| P5G | 25.0 | | | | |
| | | | Properties | | |
| Hardness (mm) | 14.4 | 14.2 | 13.7 | 14.2 | 16.9 |
| Clarity (% T) | 13.2 | 26.6 | 27.5 | 15.0 | 8.7 |
| Clarity (visual score) | 7 | 6 | 4 | 1 | 0 | nd indicates the property was not determined.

From Table 8, it can be seen that a comparatively soft stick was obtainable using an extremely low concentration of structurant according to the present invention, a stick having excellent clarity. Sticks containing GP-1 as co-structurant were harder, and still retained acceptable clarity. Sticks with similar hardness were obtainable with the incorporation of dibenzylidene sorbitol.

Example 5

Opaque Emulsion Sticks

In a first step in making opaque emulsion sticks according the present invention, a solution of the selected invention structurant, and if present GP1, in ISA was made by the same method as in the process for making suspension sticks (Example 3). The remaining water immiscible carrier oils together with an emulsifier, Abil EM 90, were heated to 85° C. in an oil bath whilst being shear mixed at 2500 rpm. The solution of antiperspirant active was heated to 80° C. and introduced gradually into the oil/emulsifier mixture, and the resultant mixture was kept constant by heating at 85° C. and sheared at 7500 rpm for 5 minutes. The emulsion was the mixed into the solution of the structurant solution which had been allowed to cool to ~90° C. The resultant mixture was stirred briefly to achieve complete mixing, poured into commercial 50 g stick barrels at approximately 80° C. and allowed to cool.

The formulations and properties of the sticks are summarised in Table 9 below.

TABLE 9

|  | Example No | |
| --- | --- | --- |
|  | Ex 5.1 | Ex 5.2 |
|  | % by weight | |
| Ingredient | | |
| Ex 1.1 Product | 1.5 | |
| Ex 1.2 Product | | 1.5 |
| GP-1 | | 4 |
| ISA | 29.0 | 27.0 |
| Finsolv TN | 29.0 | 27.0 |
| Zirconal 50 | 40.0 | 40.0 |
| Abil EM90 | 0.5 | 0.5 |
| Properties | | |
| Hardness (mm) | 27.8 | 17.1 |
| pay-off (g) at t$_o$ on wool | 0.66 | 0.80 |
| whiteness t = 24 hr on wool | 17 | 18 |

From Table 9, it can be seen that even though the stick in Example 5.1 was comparatively soft for a stick, it had acceptable pay-off and only a low visible deposit. Visually it was slightly translucent. The somewhat harder stick of Example 5.2 also gave an acceptable pay-off and low visible deposits.

Example 6

Clear Emulsion Stick

In this Example, the general method of making emulsion sticks described in Example 5 was followed, preceded by a preparatory step for refractive index matching in order to obtain a translucent emulsion stick.

In the preparatory step, the refractive indices of the ingredients of the organic and aqueous phases in the emulsion were obtained or measured, and proportions of those ingredients estimated, based on calculation and measurement, such that the two phases had roughly matched refractive indices. The two phases containing the estimated proportions of ingredients were prepared, their refractive indices measured and the proportions of the carrier oils in the continuous (water-immiscible) phase were adjusted to the extent necessary to more closely match the RI of the disperse aqueous phase.

The Versamid polymer when employed was dissolved simultaneously with the DOPAD. Any silica was incorporated in suspension in a fraction of the water-immiscible oil(s) and any antiperspirant active supplied as a solid was first dissolved in the specified weight of water.

In Examples 6.10 and 6.11, a fraction of ISA (7.4 parts for 6.10 and 5.9 parts for 6.11), all of the DC245 and the Arlacel P135™ were combined in a beaker and warmed to about 40° C. to dissolve the Arlacel. The preformed aqueous solution of Reach 908 was then poured into the Arlacel P135 solution while stirring with an overhead mixer. The speed of the mixer was increased to 1500 rpm for two minutes to form an emulsion whereupon the aqueous solution forms the internal phase. The emulsion was covered and warmed to 55-58° C. The DOPAD and the remaining ISA were combined in a beaker together with the propane-1,2-diol, di-(propane-1,2-diol), Dowanol TPnB™ and Finsolv TN™ (as appropriate) and heated to 135-140° C. on a hotplate with stirred to dissolve the DOPAD. The hotplate was then removed and the solution allowed to cool to 65-70° C. without stirring. The resultant solution was then poured into the emulsion and the mixture stirred briefly to ensure complete mixing. The mixture was then poured into a stick barrel and allowed to cool under ambient conditions. The formulation and its properties are summarised in Table 10 below.

TABLE 10

| | Example No | | | | | |
| --- | --- | --- | --- | --- | --- | --- |
| Ingredients | 6.1 | 6.2 | 6.3 | 6.4 | 6.5 | 6.6 |
| | % by weight | | | | | |
| Ex 1.2 | 1.5 | 2.0 | 2.0 | 1.5 | 2.0 | 2.0 |
| ISA | 21.14 | 12.84 | 18.51 | 20.92 | 43.45 | 42.66 |
| Finsolv TN | 5.71 | 8.22 | 5.05 | 5.65 | | |
| DC245 | 21.14 | 26.83 | 20.44 | 20.93 | 11.77 | 11.56 |
| Glycerol | 10.0 | 17.0 | 10.0 | 10.0 | | |
| Benzyl Alcohol | | 4.61 | | | | |
| Zirconal 50 | 40.0 | 40.0 | 40.0 | 40.0 | | |
| water | | | | | 16.52 | 17.58 |
| Rezal 36GP | | | | | 24.77 | |
| Reach 908 | | | | | | 23.71 |
| Abil EM90 | 0.5 | 0.5 | 1.0 | 1.0 | 0.49 | 0.49 |
| Fragrance | | | | | 1.0 | |
| Versamid 930 | | | | | | 1.0 |
| HDK H3ORX | | | | | | 1.0 |
| Properties | | | | | | |
| Hardness (mm) | 18.6 | n/d | 13.4 | 11.9 | 17.2 | 14.4 |
| Clarity (% T) | 6.7 | n/d | n/d | n/d | n/d | 42.0 |
| Clarity (visual score) | 1 | n/d | n/d | n/d | n/d | 4 |
| pay-off (g) at t$_o$ on wool) | 1.39 | n/d | n/d | n/d | n/d | n/d |

| | Example No | | | | | |
| --- | --- | --- | --- | --- | --- | --- |
| Ingredients | 6.7 | 6.8 | 6.9 | 6.10 | 6.11 | 6.12 |
| | % by weight | | | | | |
| Ex 1.2 | 2.0 | 2.0 | 1.5 | 1.5 | 1.9 | 2.0 |
| ISA | 41.08 | 43.05 | 20.6 | 21.65 | 42.7 | 32.5 |
| Finsolv TN | | | 5.55 | 3.95 | | 7.4 |
| DC245 | 11.14 | 11.67 | 20.60 | 21.65 | 10.6 | 15.1 |
| Glycerol | | | 10.0 | 10.0 | | |
| propane-1,2-diol | | | | | 4.6 | 2.1 |

TABLE 10-continued

| | | | | | | |
|---|---|---|---|---|---|---|
| di (propane-1,2-diol) | | | | | | 4.1 |
| Dowanol TPnB | | | | | 4.6 | |
| Zirconal 50 | | | 40.0 | 40.0 | | |
| water | 17.78 | 17.78 | | | 13.9 | 14.0 |
| Reach 908 | 23.71 | 23.71 | | | 20.7 | 20.8 |
| Abil EM90 | 0.49 | 0.49 | 0.75 | 0.75 | | |
| Arlacel P135 | | | | | 1.0 | 1.0 |
| Fragrance | | | | | | 1.0 |
| Versamid 930 | 2.0 | 1.0 | 1.0 | | | |
| HDK H30 | | 0.50 | | | | |
| HDK H30RX | 2.0 | | | | | |
| HDK H18 | | | | 0.5 | | |
| Properties | | | | | | |
| Hardness (mm) | 19.9 | 17.2 | 14.8 | 14.7 | 17.6 | 17.1 |
| Clarity (% T) | 19.0 | 58.4 | 0.82 | 0.74 | n/d | n/d |
| Clarity (visual score) | −1 | 7 | n/d | n/d | n/d | n/d |

Stick Characterisation-Measurement of Properties i) Stick Hardness-Penetrometer

The hardness and rigidity of a composition which is a firm solid can be determined by penetrometry. If the composition is a softer solid, this will be observed as a substantial lack of any resistance to the penetrometer probe. A suitable procedure is to utilises a lab plant PNT penetrometer equipped with a Seta wax needle (weight 2.5 grams) which has a cone angle at the point of the needle specified to be 90°10'±15'. A sample of the composition with a flat upper surface is used. The needle is lowered onto the surface of the composition and then a penetration hardness measurement is conducted by allowing the needle with its holder to drop under a total weight, (i.e. the combined weight of needle and holder) of 50 grams for a period of five seconds after which the depth of penetration is noted. Desirably the test is carried out at a number of points on each sample and the results are averaged. Utilising a test of this nature, an appropriate hardness for use in an open-ended dispensing container is a penetration of less than 30 mm in this test, for example in a range from 2 to 30 mm. Preferably the penetration is in a range from 5 mm to 20 mm.

In a specific protocol for this test measurements on a stick were performed in the stick barrel. The stick was wound up to project from the open end of the barrel, and then cut off to leave a flat, uniform surface. The needle was carefully lowered to the stick surface, and then a penetration hardness measurement was conducted. This process was carried out at six different points on the stick surface. The hardness reading quoted is the average value of the 6 measurements.

ii) Deposition by Firm Sticks (Pay-off)

Another property of a composition is the amount of it which is delivered onto a surface when the composition is drawn across that surface (representing the application of a stick product to human skin), sometimes called the pay-off. To carry out this test of deposition when the composition is a firm stick, able to sustain its own shape, a sample of the composition with standardised shape and size is fitted to apparatus which draws the sample across a test surface under standardised conditions. The amount transferred to the surface is determined as an increase in the weight of the substrate to which it is applied. If desired the colour, opacity or clarity of the deposit may subsequently be determined. A specific procedure for such tests of deposition and whiteness applicable to a firm solid stick used apparatus to apply a deposit from a stick onto a substrate under standardised conditions and then measures the mean level of white deposits using image analysis.

The substrates used were:
a: 12×28 cm strip of grey abrasive paper (3M™ P800 WetorDry™ Carborundum paper)
b: 12×28 cm strip of black Worsted wool fabric. The substrates were weighed before use. The sticks were previously unused and with domed top surface unaltered.

The apparatus comprised a flat base to which a flat substrate was attached by a clip at each end. A pillar having a mounting to receive a standard size stick barrel was mounted on an arm that was moveable horizontally across the substrate by means of a pneumatic piston.

Each stick was kept at ambient laboratory temperature overnight before the measurement was made. The stick was advanced to project a measured amount from the barrel. The barrel was then placed in the apparatus and a spring was positioned to biassed the stick against the substrate with a standardised force. The apparatus was operated to pass the stick laterally across the substrate eight times. The substrate was carefully removed from the rig and reweighed. The whiteness of the deposit could subsequently be measured as described at (v) below.

iii) Whiteness of Deposit

The deposits from the at test (ii) above, were assessed for their whiteness shortly after application (ie within 30 minutes) or after an interval of 24 hours approximately.

This was done using a Sony XC77 monochrome video camera with a Cosmicar 16 mm focal length lens positioned vertically above a black table illuminated from a high angle using fluorescent tubes to remove shadowing. The apparatus was initially calibrated using a reference white card, after the fluorescent tubes had been turned on for long enough to give a steady light output. A cloth or Carborundum paper with a deposit thereon from the previous test was placed on the table and the camera was used to capture an image. An area of the image of the deposit was selected and analysed using a Kontron IBAS™ image analyser. This notionally divided the image into a large array of pixels and measured the grey level of each pixel on a scale of 0 (black) to 255 (white). The average of the grey intensity was calculated. This was a measure of the whiteness of the deposit, with higher numbers indicating a whiter deposit. It was assumed that low numbers show a clear deposit allowing the substrate colour to be seen.

iv) Clarity of Formulation-Light Transmission

The translucency of a composition may be measured by placing a sample of standardised thickness in the light path of a spectrophotometer and measuring transmittance, as a percentage of light transmitted in the absence of the gel.

This test was carried out using a dual-beam Perkin Elmer Lambda 40 spectrophotometer. The sample of composition was poured hot into a 4.5 ml cuvette made of poly(methylmethacrylate) (PMMA) and allowed to cool to an ambient temperature of 20-25° C. Such a cuvette gives a 1 cm thickness of composition. Measurement was carried out at 580 nm, with an identical but empty cuvette in the reference beam of the spectrophotometer, after the sample in the cuvette had been held for 24 hours. A transmittance measured at any temperature in the range from 20-25° C. is usually adequately accurate, but measurement is made at 22° C. if more precision is required.

v) Clarity of Formulation-Visual Assessment Score

A gel contained within a 1 cm thick cuvette was placed directly on to a sheet of white paper on which 21 sets of figures where printed in black. The size and thickness of the figures varied systematically and were numbered from −12 (the largest, thickest set) through 0 to 8 (the smallest thinnest set) The score given to each gel was the highest numbered set which could be read clearly through the gel, the higher the number, the higher the clarity.

We claim:
1. An antiperspirant composition comprising:
   i) an antiperspirant active material;
   ii) a continuous phase which comprises water immiscible liquid carrier comprising a silicone oil and/or a non-silicone hydrophobic organic liquid selected from hydrocarbons, hydrophobic aliphatic esters, aromatic esters, hydrophobic alcohols and hydrophic ethers, and
   iii) a structurant therein which comprises a cyclodipeptide derivative, hereinafter DOPAD, having the general formula

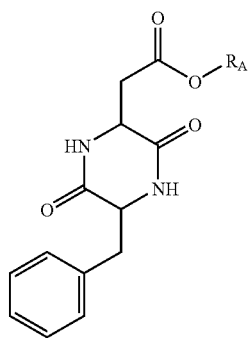

in which $R_A$ represents a carbocyclic or heterocyclic group containing not more than 2 rings, which group is substituted by at least one alkyl, alkenyl, ether or ester substituent and/or contains at least one degree of ring unsaturation and where $R_A$ is other than unsubstituted cyclohexyl; and wherein if the ring in $R_A$ is a substituted cyclohexyl group that contains an alkyl group that is methyl, the cyclohexyl group contains at least one additional alkyl group that may be the same or different.

2. A composition according to claim 1 in which $R_A$ in DOPAD represents a six membered ring, optionally bridged, other than unsubstituted cyclohexyl.

3. A composition according to claim 1 in which $R_A$ in DOPAD represents a substituted carbocyclic saturated, unsaturated non-aromatic or aromatic ring.

4. A composition according to claim 3 in which $R_A$ in DOPAD represents a single ring.

5. A composition according to claim 4 in which the ring in $R_A$ is a substituted cyclohexyl group.

6. A composition according to claim 4 in which the ring in $R_A$ is a cyclohexenyl group, optionally substituted.

7. A composition according to claim 4 in which the ring in $R_A$ is a phenyl group, optionally substituted.

8. A composition according to claim 1 in which the ring in $R_A$ is a naphthenyl group, optionally substituted.

9. A composition according to claim 1 in which $R_A$ in DOPAD represents a saturated heterocyclic ring.

10. A composition according to claim 4 in which the hetero atom in the ring in $R_A$ is nitrogen.

11. A composition according to claim 1 in which the ring in $R_A$ is substituted by at least one alkyl group.

12. A composition according to claim 11 in which the alkyl group is methyl or isopropyl.

13. A composition according to claim 11 in which the ring in $R_A$ is substituted by two to four alkyl groups.

14. A composition according to claim 11 in which at least one of the alkyl groups is methyl.

15. A composition according to claim 14 in which the ring in $R_A$ is also substituted by an isopropyl group.

16. A composition according to claim 15 in which the ring in $R_A$ is a cyclohexane or benzene ring substituted by a methyl and an isopropyl group that are para to each other.

17. A composition according to claim 1 in which the ring in $R_A$ is substituted by an hydroxyl, ether or ester substituent.

18. A composition according to claim 14 in which the DOPAD is derivable from methyl substituted piperidinol.

19. A composition according to claim 12 in which the residue $R_A$ is derivable from thymol, isopinocamphenol or a 3,5-dialkyl cyclohexanol.

20. A composition according to claim 19 in which the 3,5-dialkyl cyclohexanol is 3,5-dimethyl cyclohexanol.

21. A composition according to claim 19 in which the residue $R_A$ is derivable from thymol.

22. A composition according to claim 6 in which the residue $R_A$ is derivable from carveol.

23. A composition according to claim 7 in which the residue $R_A$ is derivable from carvacrol.

24. A composition according to claim 1 in which the DOPAD is present at a concentration of from 0.1 to 15% by weight of the composition.

25. A composition according to claim 24 in which the DOPAD is present at a concentration of from 0.3 to 10% by weight of the composition.

26. A composition according to claim 25 in which the DOPAD is present at a concentration of from 0.5 to 3.5% by weight of the composition.

27. A composition according to claim 26 in which the DOPAD is present at a concentration of from 0.4 to 8% by weight of the continuous water-immiscible phase.

28. A composition according to claim 27 in which the DOPAD is present at a concentration of from 1.5 to 2.5% by weight of the continuous water-immiscible phase.

29. A composition according to claim 26 in which the residue $R_A$ in the DOPAD is derived from thymol.

30. A composition according to claim 1 wherein the water-immiscible carrier liquid contains silicone oil in an amount which is at least 10% by weight of the composition.

31. A composition according to claim 1 which contains not more than 3% by weight of any fatty alcohol which is solid at 20° C.

32. A composition according to claim 1 which does not contain more than 3% of any wax material which is solid at 30° C., softens and is molten and soluble in the water-immiscible liquid at 95° C.

33. A composition according to claim 1 in which the DOPAD is employed in conjunction with a further structurant.

34. A composition according to claim 33 in which the further structurant is an N-acyl amino acid derivative, andlor an hydroxystearic acid andlor a dibenzylidene alditol.

35. A composition according to claim 34 in which the further structurant is N-lauroyl glutamic acid dibutylamide.

36. A composition according to claim 33 in which the further structurant is employed in a weight ratio to DOPAD of from 1:10 to 10:1.

37. A composition according to claim 36 in which the further structurant comprises N-lauroyl glutamic acid dibutylamide or 12-hydroxy stearic acid in a weight ratio to DOPAD of from 1:1 to 6:1.

38. A composition according to claim 36 in which the further structurant comprises dibenzylidene sorbitol in a weight ratio to DOPAD of from 1:3 to 1:10.

39. A composition according to claim 1 in which the composition comprises a suspension of the antiperspirant active in the water immiscible carrier liquid.

40. A composition according to claim 39 in which the carrier liquid and the suspended cosmetic active have matched refractive indices and has a light transmission of at least 1%.

41. A composition according to claim 1 wherein the composition is an emulsion with the antiperspirant active in solution in a hydrophilic disperse phase.

42. A composition according to claim 41 wherein the disperse phase contains a diol or polyol.

43. A composition according to claim 42 wherein the disperse phase contains glycerol or 1,2-propane diol.

44. A composition according to claim 41 in which the composition contains from 0.1% to 10% by weight of a nonionic emulsifier.

45. A composition according to claim 44 in which the emulsifier is an alkyl dimethicone copolyol.

46. A composition according to claim 41 in which the refractive indices of the disperse and continuous phases of the emulsion are matched.

47. A composition according to claim 1 in which the antiperspirant active comprises an aluminium and/or zirconium halohydrate, an activated aluminium and/or zirconium halohydrate, or an aluminium and/or zirconium complex or an activated aluminium and/or zirconium complex.

48. A composition according to claim 1 in which the antiperspirant active comprises complex that contains both aluminium and zirconium.

49. A composition according to claim 1 which contains from 5 to 40% by weight of the antiperspirant active.

50. An cosmetic product comprising a dispensing container having an aperture for delivery of a stick, means for urging the contents of the container to the said aperture or apertures, and a composition according to claim 1 accommodated within the container.

51. A product according to claim 50 wherein the composition is a firm gel such that a penetrometer needle with a cone angle of 9 degrees 10 minutes, drops into the gel for no more than 30 mm when allowed to drop under a total weight of 50 grams for 5 seconds.

52. A process for the production of a composition according to claim 1 comprising the steps of:
   a1) incorporating into a water-immiscible liquid carrier a structurant which is one or more structurant compounds as defined in claim 1,
   a2) mixing the liquid carrier with a solid or a disperse liquid phase comprising cosmetic active in particulate or dissolved form to be suspended in the water-immiscible liquid,
   a3) heating the liquid carrier or a mixture containing it to an elevated temperature at which the structurant is dissolved or dispersed in the water-immiscible liquid carrier
steps a1) a2) and a3) being conducted in any order followed by:
   b1) introducing the mixture into a mould which is a dispensing container, and then
   c1) cooling or permitting the mixture to cool to a temperature at which the liquid carrier is solidified.

53. A process according to claim 52 in which the DOPAD structurant is dissolved in one component of the liquid hydrophobic carrier at a temperature that is higher than that attained by the remainder of hydrophobic carrier.

54. A method for reducing perspiration on human skin comprising topically applying to the skin a antiperspirant composition according to claim 1.

55. A composition according to claim 1 wherein the composition is an emulsion with the antiperspirant active in solution in a hydrophilic, water-miscible, disperse phase.

56. An antiperspirant composition comprising:
   i) an antiperspirant active material;
   ii) a continuous phase which comprises water immiscible liquid carrier
   iii) a structurant which comprises a cyclodipeptide derivative having the general formula:

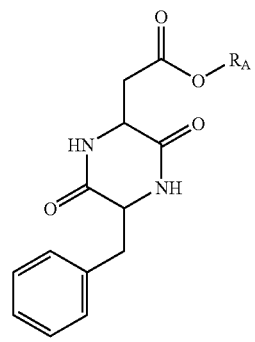

in which $R_A$ comprises a carbocyclic or heterocyclic group containing not more than 2 rings, which carbocyclic group or heterocyclic group is selected from the group consisting of: a cyclohexenyl group, optionally substituted; a phenyl group, optionally substituted; a naphthenyl group, optionally substituted, and a saturated heterocyclic ring.

57. An antiperspirant composition comprising:
   i) an antiperspirant active material;
   ii) a continuous phase which comprises water immiscible liquid carrier iii) a structurant which comprises a cyclodipeptide derivative having the general formula:

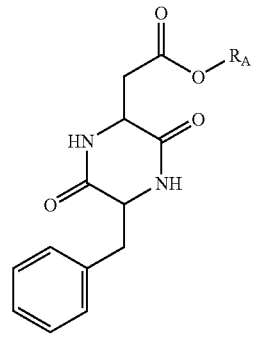

in which $R_A$ represents a carbocyclic or heterocyclic group containing not more than 2 rings, wherein the cyclodipeptide derivative is further characterized by one or more of the following:

the ring in $R_A$ is substituted by two to four alkyl groups, or the ring in $R_A$ is substituted by a methyl and an isopropyl group, or the ring in $R_A$ is substituted by an hydroxyl, ether or ester substitutent, or the ring in $R_A$ is a cyclohexane or benzene ring substituted by a methyl and an isopropyl group that are para to each other, or the residue $R_A$ is derivable from methyl substituted piperidinol, or the residue $R_A$ is derivable from thymol, isopinocamphenol, 3,5-dialkyl cyclohexanol, carveol, or carvacrol.

58. An antiperspirant composition as described in claim 1 that is transparent or translucent.

* * * * *